US009523109B2

(12) United States Patent
Uchida et al.

(10) Patent No.: US 9,523,109 B2
(45) Date of Patent: Dec. 20, 2016

(54) METHOD FOR ENZYMATICALLY PREPARING PEPTIDES FOR USE IN IMPROVEMENT OF BRAIN FUNCTION

(75) Inventors: Naoto Uchida, Kanagawa (JP); Hiroaki Goto, Kanagawa (JP); Kazuhito Ohsawa, Kanagawa (JP); Kohji Ohki, Kanagawa (JP)

(73) Assignee: CALPIS CO., LTD., Tokyo (JP)

( * ) Notice: Subject to any disclaimer, the term of this patent is extended or adjusted under 35 U.S.C. 154(b) by 447 days.

(21) Appl. No.: 13/495,581

(22) Filed: Jun. 13, 2012

(65) Prior Publication Data

US 2012/0329722 A1    Dec. 27, 2012

Related U.S. Application Data

(60) Provisional application No. 61/500,716, filed on Jun. 24, 2011.

(51) Int. Cl.
| | | |
|---|---|---|
| *C12P 21/06* | (2006.01) | |
| *A61P 25/00* | (2006.01) | |
| *A61K 38/01* | (2006.01) | |
| *A61K 38/10* | (2006.01) | |
| *A61K 38/17* | (2006.01) | |
| *C07K 14/47* | (2006.01) | |
| *A23C 9/12* | (2006.01) | |
| *A23C 9/13* | (2006.01) | |
| *A23J 3/32* | (2006.01) | |
| *A23J 3/34* | (2006.01) | |

(52) U.S. Cl.
CPC .............. *C12P 21/06* (2013.01); *A23C 9/1209* (2013.01); *A23C 9/1307* (2013.01); *A23J 3/325* (2013.01); *A23J 3/344* (2013.01); *A23L 33/18* (2016.08); *A23L 33/19* (2016.08); *A61K 38/018* (2013.01); *A61K 38/10* (2013.01); *A61K 38/1709* (2013.01); *C07K 14/4732* (2013.01); *C12Y 304/15* (2013.01); *C12Y 304/15001* (2013.01); *C12Y 304/15004* (2013.01); *C12Y 304/16* (2013.01); *C12Y 304/17* (2013.01); *C12Y 304/17001* (2013.01); *C12Y 304/21019* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 4,146,432 | A * | 3/1979 | Hirohara et al. ............. 435/180 |
| 4,684,527 | A * | 8/1987 | Motai et al. .................... 426/46 |
| 5,314,807 | A * | 5/1994 | Yoshikawa et al. ......... 435/68.1 |
| 6,908,633 | B2 * | 6/2005 | Hayasawa ............ A23C 9/1526 |
| | | | | 426/34 |
| 6,994,987 | B1 * | 2/2006 | Yamamoto et al. ......... 435/68.1 |
| 8,343,531 | B2 * | 1/2013 | Morifuji ............... A23L 1/3051 |
| | | | | 424/439 |
| 8,367,614 | B2 * | 2/2013 | Hatori ................... A23L 1/3051 |
| | | | | 514/16.6 |
| 2007/0054352 | A1 * | 3/2007 | van der Burg-Koorevaar .. A23C 9/1209 |
| | | | | 435/68.1 |
| 2011/0082281 | A1 | 4/2011 | Yamamoto et al. |

FOREIGN PATENT DOCUMENTS

| | | |
|---|---|---|
| EP | 2270133 A1 | 1/2011 |
| JP | 63-012791 A | 1/1988 |
| JP | 2-327 B2 | 1/1990 |
| JP | 03-031298 A | 2/1991 |
| JP | 04-208299 A | 7/1992 |
| JP | 6-22446 B2 | 3/1994 |
| JP | 6-37396 B2 | 5/1994 |
| JP | 6-128287 A | 5/1994 |
| JP | 06-197786 * | 7/1994 |
| JP | 7-32676 B2 | 4/1995 |
| JP | 2003-009785 A | 1/2003 |
| JP | 3898389 B2 | 1/2007 |
| JP | 2011-037785 A | 2/2011 |
| WO | WO96/13174 A1 | 5/1996 |
| WO | WO2005/012542 A1 | 2/2005 |
| WO | WO2006/114439 A2 | 11/2006 |
| WO | WO2010/077988 A2 | 7/2010 |

OTHER PUBLICATIONS

Barrett et al., Biochem. J. Lett., vol. 231, p. 807.*
Barrett et al., Biochem. J. Lett., vol. 237, p. 935.*
Introduction to the New Zealand Dairy Industry, retrieved from http://nzic.org.nz/ChemProcesses/dairy/3A.pdf on Apr. 17, 2016.*
Priest. Extracellular enzyme synthesis in the genus *Bacillus*. Bacteriol Rev. Sep. 1977;41(3):711-53.*
Crewther et al. The sequence of appearance and some properties of the enzymes liberated during growth. Australian journal of biological sciences. Aug. 1953;6(3):410-27.*
De Vries et al. Aspergillus Enzymes Involved in Degradation of Plant Cell Wall Polysaccharides. Microbiol Mol Biol Rev. Dec. 2001; 65(4): 497-522.*
Bartus, R. T., et al., "The Cholinergic Hypothesis of Geriatric Memory Dysfunction," Science 1982;217:408-414.

(Continued)

*Primary Examiner* — Gregory S Emch
(74) *Attorney, Agent, or Firm* — Cermak Nakajima & McGowan LLP; Tomoko Nakajima

(57) ABSTRACT

The invention provides a method for preparing a peptide for improving brain function, comprising hydrolyzing milk casein with an enzymatic catalyst comprising a protease to produce a hydrolysate comprising: (i) a peptide consisting of the amino acid sequence shown in SEQ ID NO: 1 or a variant thereof; (ii) a peptide consisting of the amino acid sequence shown in SEQ ID NO: 2 or a variant thereof; or (iii) a mixture of the peptides of (i) and (ii), wherein the production yield of each of the peptides is 2% or more, or the total production yield of the mixture is 10% or more. The invention also provides a food or drink or a pharmaceutical composition containing the hydrolysate.

13 Claims, 8 Drawing Sheets

(56) References Cited

OTHER PUBLICATIONS

International Search Report for PCT Patent App. No. PCT/JP2012/064997 (Jul. 10, 2012).
Supplementary European Search Report for European Patent App. No. 12803193.7 (Jan. 26, 2015).
Kim, H.-S., et al., "Angiotensin-I Converting Enzyme Inhibitory Properties of Bovine Casein Hydrolysates in Different Enzymatic Hydrolysis Conditions," Korean J. Food Sci. Ani. Resour. 2002;22(1):87-93.
Masuda, T., et al., "Improvement of the growth of Lactobacillus acidophilus in milk by addition of enzymatically digested casein," Milchwissenschaft 2003;58(314):124-127.
Yamamoto, N., et al., "Antihypertensive peptides derived from milk proteins," Nahrung—Food, VCH Verlasgsgesellschaft, Weinheim, XX, vol. 43, No. 3, 1999, pp. 159-164.
Otte, J., et al., "Influence of fermentation temperature and autolysis on ACE-inhibitory activity and peptide profiles of milk fermented by selected strains of Lactobacillus helveticus and Lactococcus lactis," International Dairy Journal 2011;21:229-238.
Office Action from Japanese Patent App. No. 2011-141101 (Sep. 24, 2014).
Anonymous: "BRENDA—Advances Search", Nov. 18, 2015, XP055229270, Retrieved from the internet: URL: http://www.brenda-enzymes.org/advanced.php?show=results&CheckOS=1&StypeOS=1&SvalueOS=&Check1%5B0%5D=. . . .
Communication Pursuant to Article 94(3) EPC for European Patent App. No. 12803193.7 (Nov. 25, 2015).

\* cited by examiner

METHOD FOR ENZYMATICALLY PREPARING PEPTIDES FOR USE IN IMPROVEMENT OF BRAIN FUNCTION

CROSS-REFERENCE TO RELATED APPLICATION

The present application claims a benefit of U.S. Provisional Application Ser. No. 61/500,716 filed on Jun. 24, 2011, the content of which is hereby incorporated by reference into this application.

BACKGROUND OF THE INVENTION

Field of the Invention

The present invention relates to a method for enzymatically preparing a peptide for improving brain function, especially a peptide for improving or preventing amnesia. Specifically, it relates to a method which involves hydrolyzing milk casein with an enzymatic catalyst comprising a protease to prepare a hydrolysate rich in a peptide having the above action.

The present invention also relates to a food or drink or a pharmaceutical composition comprising the above hydrolysate.

Background Art

Symptoms and diseases caused by decreased brain function include depression, schizophrenia, deliria, and dementias (such as cerebrovascular dementia and Alzheimer disease). Particularly, an increase in dementia patients has become a major social problem with the aging of modern society. The symptoms of dementia depend on individuals. Examples of symptoms observed in common include memory disorder, disorientation, and decreased ability to judge/think. Among dementias, those from which many patients suffer are cerebrovascular dementia and Alzheimer disease. For example, for cerebrovascular dementia, cognition/memory disorder appears because decreased cerebral blood flow damages neuronal cells in the cerebral cortex and the hippocampus. Thus, a drug improving cerebral blood flow and a drug protecting cerebral neurons are applied in addition to treating underlying diseases including hypertension, diabetes, and hypercholesterolemia which potentially cause cerebrovascular disorder. For Alzheimer disease, whose cause remains to be clearly elucidated, the decreased function of cholinergic nerve is considered to be one of the causes thereof because a decrease in the level of acetylcholine as an intracerebral neurotransmitter is observed in patients with the disease (for example, Bartus, R. T. et al., Science, 217: 408-414 (1982)). Therefore, for Alzheimer disease, a therapeutic method is predominant which is intended to prevent the decrease of function of cholinergic nerve by increasing the level of acetylcholine.

Currently, as therapeutic drugs for Alzheimer disease are commercially available, for example, acetylcholinesterase inhibitors such as donepezil hydrochloride. However, acetylcholinesterase inhibitors such as donepezil hydrochloride have a disadvantage that they cannot be administered for a long period of time because of their liver toxicity and strong side effects and are also expensive.

As a report on a peptide having the effect of improving amnesia, it is reported, for example, that lateral ventricular injection or oral administration of 300 mg/kg of XPLPR (where X is L, I, M, F, or W) has the effect of improving scopolamine-induced amnesia, suggesting the release of acetylcholine through brain C3a receptor as one of mechanisms therefor (JP Patent No. 3898389). Scopolamine is considered to cause a decrease of the function of cholinergic nerve as a muscarinic receptor antagonist, and act as an agent inducing brain dysfunction; for an improving action in a model animal for the development of therapeutic drugs for Alzheimer disease, the effect of improving and/or enhancing brain function can be demonstrated, for example, by a behavioral test such as a Y-shaped maze test, an eight-arm maze test, or a passive avoidance test. However, each of the peptides is required to be orally administered at a large dose or intraperitoneally administered, intraventricularly injected, or by other delivery route to exhibit the action, and does not have a sufficient effect as an orally ingestable substance. There is also no report in which the peptide and analogs thereof according to the present invention have been evaluated, and the action thereof involved in improving brain function has been unknown.

Thus, with the progress of the aging of the society, there is a strong need for the development of such a pharmaceutical product as to have the effect of preventing and also improving symptoms or diseases caused by decreased brain function and further a safer compound excellent in application to food.

Meanwhile, it is reported that the hydrolysate obtained by hydrolyzing casein with an enzyme has pharmacological actions such as a blood-pressure-lowering action, a smooth muscle-contracting action, and an anemia-improving action, and can be used in a nutrient preparation and a mother's milk substitute, and the like (International Publication WO 96/13174, JP Patent Publication (Kokai) No. 06-128287 (1994), JP Patent Nos. 1893866 and 1572761, U.S. Patent No. 6,994,987, JP Patent Publication (Kokoku) No. 07-032676 B (1995), and JP Patent No. 1907911); however, no report on the brain function-improving action thereof is found.

SUMMARY OF THE INVENTION

An object of the present invention is to provide a method for enzymatically preparing a new peptide for improving brain function.

Another object of the present invention is to provide a reaction product prepared by the method, and a food or drink and a pharmaceutical composition comprising the same.

In summary, the present invention has the following features.

(1) A method for preparing a peptide for improving brain function, comprising:

hydrolyzing milk casein with an enzymatic catalyst comprising a protease to produce a hydrolysate comprising:

(i) a peptide consisting of the amino acid sequence shown in SEQ ID NO: 1, or a peptide consisting of an amino acid sequence comprising deletion, substitution, or addition of one or two amino acid residues in the amino acid sequence of SEQ ID NO: 1;

(ii) a peptide consisting of the amino acid sequence shown in SEQ ID NO: 2, or a peptide consisting of an amino acid sequence comprising deletion, substitution, or addition of one or two amino acid residues in the amino acid sequence of SEQ ID NO: 2; or (iii) a mixture of the peptides of (i) and (ii), wherein the production yield of each of the peptides is 2% or more, or the total production yield of the mixture is 10% or more.

(2) The method according to (1) above, wherein the protease is a neutral protease or an alkaline protease.

(3) The method according to (1) or (2) above, wherein the protease is derived from a microorganism.

(4) The method according to (3) above, wherein the microorganism is a microorganism belonging to the genus *Bacillus* or genus *Aspergillus*, or a lactic acid bacterium.

(5) The method according to (4) above, wherein the microorganism is selected from the group consisting of *Bacillus licheniformis, Aspergillus* sp., *Aspergillus oryzae, Aspergillus melleus, Lactobacillus helveticus, Lactobacillus bulgaricus*, and *Streptococcus thermophilus*.

(6) The method according to any of (1) to (5) above, wherein the milk casein is cow milk casein.

(7) The method according to any of (1) to (6) above, wherein the production yield of the peptide consisting of the amino acid sequence shown in SEQ ID NO: 1 or the peptide consisting of an amino acid sequence comprising deletion, substitution, or addition of one or two amino acid residues in the amino acid sequence of SEQ ID NO: 1 is 5 to 10%, or more.

(8) The method according to any of (1) to (7) above, wherein the production yield of the peptide consisting of the amino acid sequence shown in SEQ ID NO: 2 or the peptide consisting of an amino acid sequence comprising deletion, substitution, or addition of one or two amino acid residues in the amino acid sequence of SEQ ID NO: 2 is 10 to 50%, or more.

(9) The method according to any of (1) to (8) above, wherein the total production yield of the peptide consisting of the amino acid sequence shown in SEQ ID NO: 1 or the peptide consisting of an amino acid sequence comprising deletion, substitution, or addition of one or two amino acid residues in the amino acid sequence of SEQ ID NO: 1 and the peptide consisting of the amino acid sequence shown in SEQ ID NO: 2 or the peptide consisting of an amino acid sequence comprising deletion, substitution, or addition of one or two amino acid residues in the amino acid sequence of SEQ ID NO: 2 is 15 to 60%, or more.

(10) The method according to any of (1) to (9) above, wherein the hydrolysate further comprises a peptide consisting of the amino acid sequence shown in SEQ ID NO: 3 or a peptide consisting of an amino acid sequence comprising deletion, substitution, or addition of one or two amino acid residues in the amino acid sequence of SEQ ID NO: 3.

(11) The method according to any of (1) to (10) above, wherein the enzymatic catalyst further comprises an enzyme having a peptidase activity.

(12) The method according to any of (1) to (11) above, wherein the enzymatic catalyst is immobilized on a support.

(13) The method according to any of (1) to (12) above, wherein the hydrolysis of the milk casein is carried out using milk.

(14) The method according to any of (1) to (13) above, wherein weight ratio of the enzyme/milk casein is 1/100 to 1/1,000.

(15) The method according to any of (1) to (14) above, wherein reaction time of the hydrolysis reaction at 45 to 55° C. is 2 to 10 hours.

(16) The method according to any of (1) to (15) above, further comprising inactivating the enzymatic catalyst.

(17) The method according to any of (1) to (16) above, further comprising isolating and/or concentrating the peptide consisting of the amino acid sequence shown in SEQ ID NO: 1 or the peptide consisting of an amino acid sequence comprising deletion, substitution, or addition of one or two amino acid residues in the amino acid sequence of SEQ ID NO: 1, the peptide consisting of the amino acid sequence shown in SEQ ID NO: 2 or the peptide consisting of an amino acid sequence comprising deletion, substitution, or addition of one or two amino acid residues in the amino acid sequence of SEQ ID NO: 2, the peptide consisting of the amino acid sequence shown in SEQ ID NO: 3 or the peptide consisting of an amino acid sequence comprising deletion, substitution, or addition of one or two amino acid residues in the amino acid sequence of SEQ ID NO: 3, or a mixture comprising at least two of the peptides.

(18) A hydrolysate produced by the method according to any of (1) to (17), comprising at least one of the peptides consisting of the amino acid sequences shown in SEQ ID NOS: 1 to 3 or the peptides consisting of amino acid sequences comprising deletion, substitution, or addition of one or two amino acid residues in the amino acid sequences of SEQ ID NOS: 1 to 3, in an amount of about 0.5 mg or more per gram of a dry solid of the hydrolysate.

(19) The hydrolysate according to (18) above, wherein the hydrolysate is dried.

(20) A food or drink comprising the hydrolysate according to (18) or (19) above.

(21) A supplement comprising the hydrolysate according to (18) or (19) above.

(22) The food or drink according to (20) above or the supplement according to (21) above, wherein the food or drink or the supplement is a lactic acid bacterium-fermented food or drink.

(23) The food or drink or the supplement according to any of (20) to (22) above, wherein the food or drink or the supplement is a functional food.

(24) A pharmaceutical composition comprising the hydrolysate according to (18) or (19) above and a pharmaceutically acceptable carrier.

(25) The pharmaceutical composition according to (24) above, wherein the composition is for improving brain function.

(26) The pharmaceutical composition according to (25) above, wherein the improvement of brain function is the improvement or prevention of amnesia.

The method of the present invention enables the efficient enzymatic production of a peptide having a brain function-improving action such as improving or preventing amnesia.

DETAILED DESCRIPTION OF THE INVENTION

Figure 1:
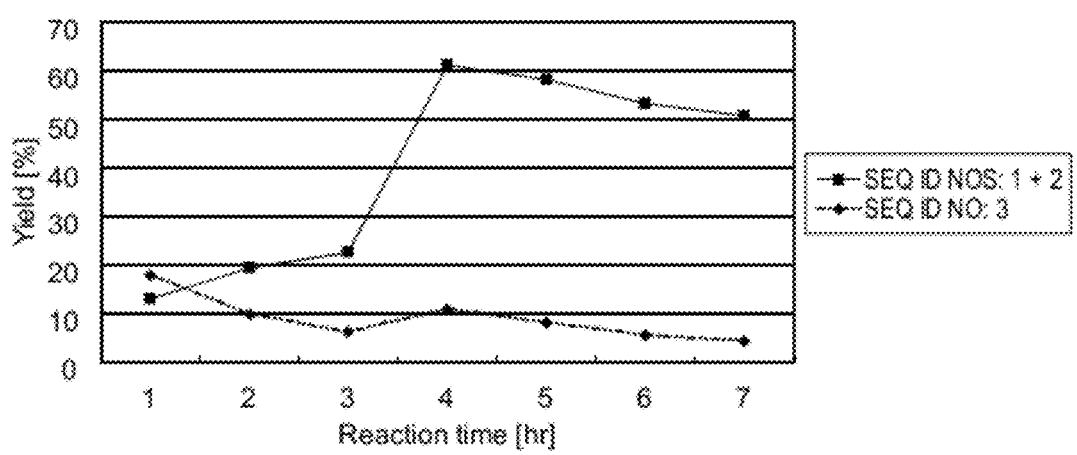
FIG. 1 is a graph showing the time course of the production yield of Asn-Ile-Pro-Pro-Leu-Thr-Gln-Thr-Pro-Val-Val-Val-Pro-Pro-Phe-Leu-Gln-Pro-Glu (NIPPLTQTPVVVPP-FLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2) and Ser-Trp-Met-His-Gln-Pro-His-Gln-Pro-Leu-Pro-Pro-Thr-Val-Met-Phe-Pro-Pro-Gln-Ser-Val-Leu (SWMHQPHQ-PLPPTV MFPPQSVL; SEQ ID NO: 3) when a *Bacillus licheniformis*-derived enzyme, Protin SD-AY10 (from Amano Enzyme Inc.), was added to a phosphate buffer solution (pH: 7.0 to 7.3) containing cow milk casein sodium to a weight ratio of enzyme/casein of 1/200 for hydrolysis reaction.

The present invention will be described in further detail.
1. Peptide Having Brain Function-Improving Action The peptides enzymatically produced from milk casein or a milk casein-containing raw material by the method of the present invention have the following amino acid sequences.

The amino acid sequence of Asn Ile Pro Pro Leu Thr Gln Thr Pro Val Val Val Pro Pro Phe Leu Gln Pro Glu (or NIPPLTQTPVVVPPFLQPE) (SEQ ID NO: 1; hereinafter also referred to as "N-E peptide") or an amino acid sequence comprising deletion, substitution, or addition of one or two amino acid residues in the amino acid sequence.

The amino acid sequence of Asn Ile Pro Pro Leu Thr Gln Thr Pro Val Val Val Pro Pro Phe Leu Gln Pro Glu Val Met (or NIPPLTQTPVVVPPFLQPEVM) (SEQ ID NO: 2; hereinafter also referred to as "N-EVM peptide") or an amino acid sequence comprising deletion, substitution, or addition of one or two amino acid residues in the amino acid sequence.

The amino acid sequence of Ser Tip Met His Gln Pro His Gln Pro Leu Pro Pro Thr Val Met Phe Pro Pro Gln Ser Val Leu (or SWMHQPHQPLPPTVMFPPQSVL) (SEQ ID NO: 3; hereinafter also referred to as "S-SVL peptide") or an amino acid sequence comprising deletion, substitution, or addition of one or two amino acid residues in the amino acid sequence.

The N-E peptide is a peptide in which the ValMet sequence is removed from C-terminus of the N-EVM peptide. The S-SVL peptide has a sequence different from the above two peptides; however, all of these peptides are peptides excised from milk casein and have the common characteristics of having a brain function-improving action, especially an amnesia-improving or -preventing action. Their amnesia-improving or -preventing action is demonstrated in Examples 4 to 7 hereinbelow.

As used herein, "brain function-improving action" refers to the effect of improving disorders associated with the decrease of brain function relating to memory and recognition.

As used herein, "amnesia" refers to memory decline and is one of memory disorders. Thus, as used herein, "improving or preventing amnesia" means improving or preventing the memory decline.

The "peptide consisting of an amino acid sequence comprising deletion, substitution, or addition of one or two amino acid residues" as used herein for the amino acid sequence of a peptide is a variant of the peptide (also referred to as "variant peptide") consisting of the amino acid sequence shown in SEQ ID NO: 1, 2, or 3, and has a brain function-improving action at the same or similar level (for example, 50% or more, preferably 80% or more, more preferably 100% or more) to the brain function-improving action of the peptide consisting of the amino acid sequence shown in SEQ ID NO: 1, 2, or 3. Such a variant peptide may also be a peptide consisting of an amino acid sequence having 89% or more, preferably 90% or more, more preferably 94% or more sequence identity with the amino acid sequence shown in SEQ ID NO: 1, 2, or 3. As used herein, "sequence identity" refers to the percentage (%) of the number of identical amino acid residues to the total number of amino acids including the number of gaps when two amino acid sequences are aligned so as to maximize the match of amino acids therebetween by introducing gaps or by introducing no gaps. The percentage of sequence identity can be determined, for example, by using a known algorithm such as BLAST or FASTA publicly available through NCBI in USA.

Preferred examples of the variant peptide include a peptide consisting of an amino acid sequence in which the conservative amino acid substitution of one or two amino acid residues is contained in the amino acid sequence shown in SEQ ID NO: 1, 2, or 3.

As used herein, "conservative amino acid substitution" refers to substitution between amino acids similar in properties such as polarity, electric properties, and structural properties, including hydrophobic amino acids, polar amino acids, acidic amino acids, basic amino acids, amino acids having branched side chains, and aromatic amino acids. Examples of the hydrophobic (non-polar) amino acid include glycine, alanine, valine, leucine, isoleucine, and proline; examples of the polar amino acid include serine, threonine, cysteine, methionine, asparagine, and glutamine; examples of the acidic amino acid include aspartic acid and glutamic acid; examples of the basic amino acid include lysine, arginine, and histidine; examples of the amino acid having a branched side chain include valine, isoleucine, and leucine; and examples of the aromatic amino acid include phenylalanine, tyrosine, tryptophan, and histidine.

The variant peptide can encompass a variant obtained by artificially altering the amino acid sequence of the peptide of SEQ ID NO: 1, 2, or 3 in addition to a natural variant based on the difference in the source of casein as a raw material substrate. Such a variant can be synthesized by a known peptide synthesis technique, and its brain function-improving effect, particularly its amnesia-improving effect can be confirmed by an effectiveness testing method as stated in Examples hereinbelow.

The peptide of the present invention may encompass the form of a salt as well as the free form thereof. This is because when the peptide is produced, the peptide can form a salt with calcium (Ca) ion contained in casein as a raw material, for example, sodium (Na) ion derived from an alkaline solution used for dissolving casein, a metal ion derived from a buffer solution used as needed, and the like. Making the peptide in salt form is expected to facilitate the dissolution of the peptide in water.

2. Method for Enzymatically Preparing Peptide 2.1 General Procedure for Enzymatic Preparation The peptide for improving brain function according to the present invention may be produced by hydrolyzing milk casein with an enzymatic catalyst containing a protease.

Specifically, the present invention provides a method for preparing a peptide for improving brain function, comprising hydrolyzing milk casein with an enzymatic catalyst containing a protease to produce a hydrolysate containing the N-E peptide (SEQ ID NO: 1) or a variant peptide thereof, the N-EVM peptide (SEQ ID NO: 2) or a variant peptide thereof, or a mixture thereof, wherein the production yield of each of the peptides is 2% or more, preferably 5 to 10%, or more, or the total production yield of the mixture is 10% or more, preferably 15 to 60%, or more.

The milk casein may be casein of an animal milk such as cow milk, goat milk, or horse milk, and is preferably cow milk.

When milk casein is used in the enzymatic reaction, casein may be added little by little to an alkaline aqueous solution such as aqueous caustic soda for dissolution under stirring, if necessary, while heating at 50° C. or less, followed by adjusting the pH at around neutral pH with an acid such as hydrochloric acid.

Alternatively, the milk casein may be a casein-containing raw material such as milk. In this case, the alkali treatment as described above may be unnecessary.

As described in Background Art, many examples are known of the use of a hydrolysate obtained by enzymatically hydrolyzing milk protein in a pharmaceutical, a food, or the like; however, the production of the N-E peptide and/or the N-EVM peptide has not previously been reported or known. The method of the present invention is a method capable of enhancing the production yield of these new peptides.

According to the present invention, when the enzyme amount is reduced relative to the casein amount, the S-SVL peptide (SEQ ID NO: 3) or a variant peptide thereof having the same brain function-improving action is also produced together with the N-E peptide or a variant peptide thereof and the N-EVM peptide or a variant peptide thereof.

The enzymatic catalyst and reaction conditions will be described below in further detail.

2.2 Enzymatic Catalyst

The enzymatic catalyst used for hydrolyzing milk casein in the method of the present invention may be an enzymatic catalyst containing a protease. Here, the expression "comprise" or "contain" mean that the catalyst may comprise/contain, if necessary, a hydrolytic enzyme such as an enzyme having a peptidase activity, in addition to a protease.

The protease may be of any origin or type provided that it enables the production of the N-E peptide or a variant peptide thereof and/or the N-EVM peptide or a variant peptide thereof from milk casein. That is, the protease may be an enzyme capable of hydrolyzing proteins and polypeptides and, according to the present invention, encompass all proteases from microorganisms such as bacteria, yeasts, and fungi, algae, plants, animals, and others.

Among such proteases, preferred is a neutral protease or an alkaline protease. The neutral protease is a protease having the optimal pH in the neutral region, and the alkaline protease is a protease having the optimal pH in the alkaline region. The reaction pH in the method of the present invention is pH 6.5 to 8.5, preferably pH 7.0 to 8.0; thus, an enzyme is preferable which has hydrolytic activity in such a pH range.

Among the above proteases, preferred is, for example, a serine protease. This enzyme is a protease typically having catalytic triplet residues, serine, histidine, and aspartic acid, at the active center.

The protease is preferably a microorganism-derived protease enabling the production of the N-E peptide or a variant peptide thereof and/or the N-EVM peptide or a variant peptide thereof from milk casein with the above yield. For example, a protease derived from a microorganism belonging to the genus *Bacillus* or the genus *Aspergillus*, a lactic acid bacterium-derived protease, or the like may be used as the enzyme in the method of the present invention. Specifically, the preferable protease may include a protease derived from a microorganism selected from the group consisting of *Bacillus licheniformis*, *Aspergillus* sp., *Aspergillus oryzae*, *Aspergillus melleus*, *Lactobacillus helveticus*, *Lactobacillus bulgaricus*, and *Streptococcus thermophilus*. The enzyme may be in any forms such as a purified enzyme, a partially-purified enzyme, a crude enzyme, and disrupted microbial cells (preferably, a freeze-dried product), and may have the activity of excising the peptides from milk casein.

Because an enzyme has a substrate specificity, there are enzymes which may be unsuitable for the method of the present invention, including, for example, animal enzymes such as trypsin and pancreatin and proteases derived from *Bacillus amyloliquefaciens*, *Bacillus stearothermophilus*, and others as stated in Examples hereinbelow.

With a protease suitable for the method of the present invention, for example, as stated in Example 1, about 10 mg of cow milk casein sodium is dissolved in a phosphate buffer solution (pH: 7.0 to 7.3), to which a test protease is then added so as to provide a weight ratio of enzyme/casein of about 1/200 for treatment at a temperature of about 35° C. to about 50° C. for about 1 to 4 hours, followed by terminating the reaction with trichloroacetic acid; a suitable protease can be selected, for example, by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard to determine a desired peptide production.

Examples of proteases which may be used in the method of the present invention include, but not limited to, the *Bacillus licheniformis*-derived alkaline protease "Protin SD-AY10" (trade name, from Amano Enzyme Inc.) and the *Aspergillus* sp.-derived alkaline protease "Sumizyme MP" (trade name, from Shinnihon Chemicals Corporation).

The enzymatic catalyst used in the method of the present invention may further contain an enzyme having a peptidase activity. The enzyme having a peptidase activity has an activity to produce the N-E peptide or a variant peptide thereof and/or the N-EVM peptide or a variant peptide thereof from casein or an activity to produce the N-E peptide from the N-EVM peptide. In fact, as shown from the time course of peptide production in Tables 1 and 4 stated in Examples hereinbelow, the N-EVM peptide is first produced, followed by the production of the N-E peptide; thus, the N-E peptide may probably be produced from the precursor N-EVM peptide through enzymes having a peptidase activity contained in the commercial enzyme preparations actually used.

The enzyme having a peptidase activity which may be used in combination with each above protease is exemplified below.

Carboxypeptidases (EC3.4.16.-, EC3.4.17.-, EC3.4.18.-), which release one amino acid from C-terminus of a peptide, such as, for example, carboxypeptidase A (EC3.4.17.1), carboxypeptidase B (EC3.4.17.2), carboxypeptidase C (EC3.4.16.5), and carboxypeptidase Y (EC3.4.16.5). Alternatively, peptidyl dipeptidases (EC3.4.15.-), which release two amino acids from C-terminus of a peptide, such as, for example, peptidyl dipeptidase A (EC3.4.15.1), peptidyl dipeptidase B (EC3.4.15.4), and peptidyl dipeptidase Dcp (EC3.4.15.5).

Carboxypeptidase A (EC3.4.17.1) (http://www.chem.qmul.ac.uk/iubmb/enzyme/EC3/4/17/1.html) is considered to less easily degrade C-terminal -PE (-Pro-Glu) of the N-E peptide (NIPPLTQTPVVVPPFLQ-PE; SEQ ID NO: 1) because although the enzyme releases a C-terminal amino acid, it little or completely not acts on terminal -Asp, -Glu, -Arg, -Lys or -Pro, while for the N-EVM peptide (NIPPLTQTPVVVPPFLQ-PE-VM; SEQ ID NO: 2), the C-terminal-VM (-Val-Met) can be hydrolyzed to produce the N-E peptide.

Carboxypeptidase B (EC3.4.17.2) (http://www.chem.qmul.ac.uk/iubmb/enzyme/EC3/4/17/2.html) is a typical carboxypeptidase enzyme catalyzing the hydrolysis of basic amino acids; although the enzyme is not likely to directly act on the conversion of the N-EVM peptide to the N-E peptide, it can contribute to the production of these peptides.

Carboxypeptidase Y (EC3.4.16.5) (http://www.chem.qmul.ac.uk/iubmb/enzyme/EC3/4/15/1.html) can contribute to the production of peptides including the N-E peptide because it has a wide substrate specificity.

Peptidyl dipeptidase A (EC3.4.15.1) (http://www.chem.qmul.ac.uk/iubmb/enzyme/EC3/4/15/1.html) is not considered to degrade C-terminal -PE (-Pro-Glu-) of the N-E peptide (NIPPLTQTPVVVPPFLQ-PE; SEQ ID NO: 1) because it releases C-terminal dipeptide Xaa-Yaa of an oligopeptide+Xaa-Yaa (wherein Xaa is not Pro, and Yaa is not Asp or Glu), while for the N-EVM peptide (NIPPLTQT-PVVVPPFLQ-PE-VM; SEQ ID NO: 2), C-terminal -VM (-Val-Met) can be hydrolyzed to produce the N-E peptide.

Peptidyl dipeptidase B (EC3.4.15.4) (http://www.chem.qmul.ac.uk/iubmb/enzyme/EC3/4/15/4.html) can contribute to the production of peptides including the N-E peptide because it has a wide substrate specificity.

Peptidyl dipeptidase Dcp (EC3.4.15.5) (http://www.chem.qmul.ac.uk/iubmb/enzyme/EC3/4/15/5.html) can contribute to the production of peptides including the N-E peptide because it has a wide substrate specificity.

Examples of the enzyme having a peptidase activity can include endoproteinase Glu-C (EC3.4.21.19) and enzymes having the same activity in addition to the above exemplified enzymes. The enzyme is an enzyme selectively hydrolyzing the C-terminus of glutamic acid (Glu) in a protein or a peptide (http://www.chem.qmul.ac.uk/iubmb/enzyme/EC3/4/21/19. html).

The enzyme having a peptidase activity used in the method of the present invention may be in any forms such as a purified enzyme, a partially-purified enzyme, a crude enzyme, and disrupted microbial cells (preferably, a freeze-dried product) provided that it has the above enzyme activity.

The enzymatic catalyst used in the method of the present invention may be preferably a combination of at least one above-described protease and at least one above-described enzyme having a peptidase activity. In this case, the way in which these enzymes are added is not particularly limited; for example, they may be simultaneously present in the reaction system in the hydrolysis reaction, or the way is used in which the protease is first added for reaction, followed by adding the enzyme having a peptidase activity to the reaction system at the time point that the production of the N-EVM peptide or a variant peptide thereof is almost maximal.

The enzymatic catalyst may also be immobilized on a support. The support is not particularly limited provided that it can be typically used for the immobilization of enzymes. The method of binding the enzyme to the support may be based on covalent bonding or non-covalent bonding. In the case of covalent bonding, a reactive group such as cyanogen bromide, N-hydroxymaleimide, phthalaldehyde, diisocyanate, or imide ester can be bound to a support, followed by binding the enzyme to such a group. In the case of non-covalent bonding, it can be bound to a support in a way such as physical adsorption or van der Waals binding, ion binding, cross-linking, inclusion, or microcapsules. Non-limited examples of the support include minerals, metals, polymers, and polysaccharides. Minerals include, for example, pumice stone and porosity glass. Metals include, for example, magnetic substance and ceramic. Polymers include, for example, polyacrylamide gel, an ion-exchange resin, photocrosslinkable resin prepolymer, and urethane prepolymer. Polysaccharides include, for example, K-carrageenan and an alginate.

The protease and the enzyme having a peptidase activity may be together or separately immobilized to the support.

2.3 Reaction Condition

The enzymatic hydrolysis reaction may be carried out by a continuous method or a batch method. The continuous method typically uses an immobilized enzymatic catalyst, while the batch method uses a non-immobilized enzymatic catalyst.

When the immobilized enzymatic catalyst is used, the catalyst may be packed in a column whose temperature can be controlled, and a casein solution is continuously applied thereinto at a fixed flow rate. The reaction solution is sampled over time to monitor the production of a desired peptide, and the reaction solution is recovered once the highest production content is reached.

In the case of the non-immobilized enzymatic catalyst, a casein solution and an enzymatic catalyst are added to a reaction vessel equipped with a stiffer whose temperature can be controlled, reacted by a batch method to similarly monitor the production of a desired peptide, and the reaction solution is recovered once the highest production content is reached.

The milk casein as a substrate raw material may be an animal milk casein as described above, preferably cow casein, and is preferably in the form of a milk casein salt easily soluble in water, for example, milk casein sodium. Typically, the milk casein sodium may be prepared, for example, by suspending casein in water and adding aqueous caustic soda thereto little by little under stirring, or adding casein to aqueous caustic soda little by little, and, if necessary, the pH is adjusted after the addition of casein. Alternatively, in place of milk casein salt, milk containing casein may be used directly or after concentration.

Because an enzyme has an optimal pH, a buffer solution is preferably contained so that pH is not changed during reaction; however, if the control of pH is possible, the buffer solution is not always required. The buffer solution may be a buffer solution capable of maintaining a pH ranging from the neutral region to the weak alkaline region, for example, a pH of 6.5 to 8.5, preferably a pH of 7.0 to 8.0. Such buffer solutions include, for example, a phosphate buffer solution, a Tris-hydrochloric acid buffer solution, and an ammonium chloride buffer solution. The buffer solution may be added in an amount capable of showing a buffer action to a substrate raw material solution.

The weight ratio of each enzyme/milk casein may be 1/50 to 1/2,000, preferably 1/100 to 1/1,000, more preferably 1/150 to 1/250, and is, for example, 1/200. Alternatively, the ratio may be 1 to 100,000 units (U), preferably 10 to 50,000 units (U), more preferably 50 to 10,000 units (U) (where 1 U refers to the enzyme activity of degrading 1 μmol of a substrate for 1 minute) as protease per gram of milk casein. It may be adjusted depending on the type and properties of the enzyme.

The reaction temperature may be a temperature not inactivating the enzyme, and may be typically 30 to 60° C., preferably 45 to 55° C. If the enzyme is a heat-resistant enzyme, a temperature exceeding the range can also be used. Iit is preferably a temperature at which casein as a substrate is not coagulated.

The reaction time varies depending on the type of the enzyme, the temperature, and other factors. It may be typically 1 to 12 hours, preferably 2 to 10 hours, more preferably 3 to 7 hours.

The reaction is monitored, and the reaction may be performed until the production amount of a desired peptide reaches a predetermined value.

According to the method of the present invention, the production yield of the N-E peptide (SEQ ID NO: 1) or a variant peptide thereof is 2 to 10%, or more, and/or the production yield of the N-EVM peptide (SEQ ID NO: 2) or a variant peptide thereof is 10 to 50%, or more, and the total production yield of the N-E peptide or a variant peptide thereof and the N-EVM peptide or a variant peptide thereof is 15 to 60%, or more. Particularly, when the conversion of the N-EVM peptide to the N-E peptide is achieved by the action of the enzyme having a peptidase activity, the production yield of the N-E peptide may be predicted to be further increased. According to the method of the present invention, a mixture of the peptides is typically produced. It is preferable to obtain a mixture rich in the N-E peptide.

As used herein, "production yield" is the percentage (%) of the molar concentration of each produced peptide to the molar concentration calculated from the average molecular weight of β-casein. Specifically, for example, the production yield has been determined by taking the average molecular weight of β-casein in cow milk casein containing the sequences of the N-E peptide (SEQ ID NO: 1), the N-EVM peptide (SEQ ID NO: 2), and the S-SVL peptide (SEQ ID NO: 3) to be 25,100, taking the peptide molecular weight to be 2,086.4 for the N-E peptide (SEQ ID NO: 1), 2,316.8 for the N-EVM peptide (SEQ ID NO: 2) and 2,550.0 for the S-SVL peptide (SEQ ID NO: 3), and further taking the content ratio of 13-casein in the cow milk casein to be about 30%.

According to the method of the present invention, the S-SVL peptide (SEQ ID NO: 3) or a variant peptide thereof can be produced at a production yield of about 3 to 70% by using different types or amounts of the enzyme (see FIGS. 1 to 4). For example, this peptide can be produced at a yield of about 65% in about 4 hours when the enzyme preparation "Protin SD-AY10" (trade name, 90,000 PU/g or more, from Amano Enzyme Inc.) is used for hydrolysis reaction at enzyme/casein=1/1,000 (weight ratio) (see Table 5). On the other hand, it may be produced at a yield of 11% in 4 hours when the same enzyme is used at enzyme/casein=1/200 (weight ratio) for the same hydrolysis reaction (see Table 4). The yield of the S-SVL peptide decreases from about 10% to 0% with the lapse of reaction time when "Sumizyme MP" (trade name, from Shinnihon Chemicals Corporation) is used as an enzyme preparation (see Tables 6 and 7).

After the end of reaction, the enzymatic catalyst may be typically inactivated. The inactivation can be performed, for example, by heating at about 60° C. to about 75° C.

3. Hydrolysate

The present invention further provides a hydrolysate produced by the above method, containing at least any one of the peptides consisting of the amino acid sequences shown in SEQ ID NOS: 1 to 3 or peptides consisting of amino acid sequences containing deletion, substitution, or addition of one or two amino acid residues in the amino acid sequence of SEQ ID NO: 1 to 3, in an amount of about 0.5 mg or more per gram of a dry solid of the hydrolysate.

Here, "hydrolysate" generally refers to a reaction solution (preferably the reaction solution after enzyme inactivation) obtained by the hydrolysis reaction of milk casein by the above method or a concentrate thereof.

This hydrolysate is characterized by containing about 0.5 mg or more, preferably about 1.0 mg or more, more preferably about 10 to 15 mg, or more of the N-E peptide or a variant peptide thereof per gram of the dry solid of the hydrolysate.

The hydrolysate may further contain about 1.0 to 20 mg, or more of the N-EVM peptide or a variant peptide thereof per gram of a dry solid of the hydrolysate and/or about 1.0 to 20 mg, or more of the S-SVL peptide or a variant peptide thereof per gram of a dry solid of the hydrolysate.

Preferably, the total content of the N-E peptide or a variant peptide thereof and the N-EVM peptide or a variant peptide thereof in the hydrolysate may be about 1.5 to 4.0 mg, or more, preferably about 10 to 30 mg, or more per gram of a dry solid of the hydrolysate.

The hydrolysate of the present invention may be directly used, or may be concentrated by ultrafiltration or the like, or may be dried. The drying is preferably freeze drying, and may be freeze drying after concentration.

As needed, each of the N-E peptide or a variant peptide thereof, the N-EVM peptide or a variant peptide thereof, and the S-SVL peptide or a variant peptide thereof may be isolated from the hydrolysate, or the N-E peptide or a variant peptide thereof, the N-EVM peptide or a variant peptide thereof, and the S-SVL peptide or a variant peptide thereof may be separated from each other. In the latter case, the N-E peptide or a variant peptide thereof and the N-EVM peptide or a variant peptide thereof can be separated as a mixture, and the mixture may be concentrated so that it is rich in these components, preferably rich in the N-E peptide or a variant peptide thereof.

The isolation and concentration of each peptide may be performed by using a common technique, for example, techniques including gel filtration, chromatography such as ion-exchange chromatography, affinity chromatography, silica gel chromatography, or HPLC, crystallization, salting-out, organic solvent precipitation, and ultrafiltration alone or in combination. The buffer component and the like may also be removed by this operation.

4. Application to Pharmaceutical and Food

The hydrolysate or the above peptides of the present invention each have a brain function-improving action, for example, have the action to improve or prevent amnesia as well as enhancing memory. As described above, amnesia refers to memory decline and is one of memory disorders. Such an effect is demonstrated in Examples hereinbelow. Thus, the hydrolysate or the above peptides of the present invention can be used for treating or preventing symptoms and diseases caused by decreased brain function, for example, diseases or symptoms such as depression, schizophrenia, deliria, and dementias (cerebrovascular dementia, Alzheimer disease, and the like), and can also be used when amnesia symptoms are observed although such diseases are not evident.

4.1 Application to Pharmaceutical

The present invention further provides a pharmaceutical composition comprising the above hydrolysate and a pharmaceutically acceptable carrier.

The hydrolysate at least comprises the N-E peptide among the above peptides. The hydrolysate may be contained in the form of a liquid or a solid in the carrier.

According to an embodiment of the present invention, the pharmaceutical composition is for improving brain function. More specifically, the pharmaceutical composition is for improving or preventing amnesia.

Possible indications include symptoms and diseases caused by decreased brain function, for example, diseases or symptoms such as depression, schizophrenia, deliria, and dementias (cerebrovascular dementia, Alzheimer disease, and the like), as described above.

The amount of the hydrolysate as an active ingredient in the pharmaceutical composition of the present invention is not particularly limited. It may be typically preferably 0.1 µg/kg body weight to 1 mg/kg body weight in terms of the weight of each of the peptides although not being limited to the range. The dose administered may be determined according to age, sex, the degree of symptoms, and the like.

The route of administration may be, for example, oral administration, intravenous administration, transmucosal administration, intranasal administration, or intrarectal administration, and it is preferably oral administration. The administration may be performed to subjects in once daily or a plurality of times daily in divided doses.

The subject may be typically a human, and also encompasses a mammal other than a human, for example, a pet animal such as a dog.

The dosage form (or preparation) may be any form of a solid preparation and a liquid preparation; examples thereof include a tablet, a pill, a capsule, a powder, a granule, a solution, an injection, an epipastic, and an aerosol preparation.

The pharmaceutically acceptable carrier includes an excipient or a diluent; examples thereof include dextrans, saccharose, lactose, maltose, xylose, trehalose, mannitol, sorbitol, gelatin, carboxymethylcellulose, carboxyethylcellulose, hydroxypropylmethylcellulose, gum arabic, guar gum, tragacanth, acrylate copolymer, ethanol, saline, and Ringer's solution.

In addition to the above carrier, additives may be added such as a preservative, a stabilizer, a binder, a pH regulator, a buffer, a thickener, a gelling agent, and an antioxidant, if necessary. These additives may be preferably those used in preparing pharmaceutical products.

The pharmaceutical composition of the present invention may be used in combination with another pharmaceutical product having a brain function-improving effect. Examples of such pharmaceutical product include the following, and it is preferably a commercially available pharmaceutical product.

Therapeutic drugs for dementia such as, for example, an acetylcholinesterase inhibitor (donepezil, galanthamine, rivastigmine, tacrine, or the like) and an NMDA receptor antagonist (memantine or the like).

Antianxiety drugs such as, for example, a benzodiazepine antianxiety drug.

Antidepressant drugs such as, for example, a selective serotonin reuptake inhibitor (SSRI), serotonin/norepinephrine (noradrenaline) reuptake inhibitor (SNRI), a tricyclic antidepressant (TCA), a tetracyclic antidepressant, a triazolopyridine antidepressant (SARI), a monoamine oxidase inhibitor (MAO inhibitor), a noradrenergic/specific serotonergic antidepressant (NaSSA), and a norepinephrine/dopamine reuptake inhibitor (NDRI).

Antipsychotic drugs.

Hypnotics.

These pharmaceutical products can each be administered at any time point of with, before, and after the administration of the pharmaceutical composition of the present invention. The dose thereof is preferably a dose as instructed by a pharmaceutical supplier when it is a commercially available pharmaceutical product.

4.2 Application to Food or Feed

The present invention further provides a food or drink or a supplement containing the above hydrolysate.

Such a food or drink or a supplement can be a functional food or drink or a health food because the hydrolysate has a brain function-improving action, especially has an amnesia-improving or -preventing action. Examples thereof include a food or drink or a supplement obtained by adding the hydrolysate to lactic acid bacterium-fermented solution. The supplement may be one of the food classifications, consisting of a dietary supplement, and herein refers to a function auxiliary substance capable of providing a brain function-improving action.

The hydrolysate can also be used as a material for feed for a non-human animal For example, for a dog, for example, the hydrolysate may be blended upon the production of a dog food.

Examples of the food or drink include, but not limited to, various drinks, various dairy products such as yogurt, cheese, butter, and lactic acid bacterium-fermented products, liquid food, jelly, candy, retort pouched food, tablet confectionary, cookies, sponge cake, bread, biscuits, and chocolate.

The functional food or drink, the health food, or the supplement may be in the form of a solid, a gelatinous material, or a liquid, for example, may be in the form of any of various processed foods or drinks, powder, a tablet, a pill, a capsule, a jelly, a granule, or the like.

The food or drink may be properly blended with food additives such as carbohydrate, protein, lipid, vitamins, minerals, a saccharide (glucose or the like), a natural or artificial sweetener, citric acid, carbonated water, fruit juice, a stabilizer, a preservative, a binder, a thickener, and an emulsifier.

The blending amount of the hydrolysate is not particularly limited. It may be 0.1 μg/kg body weight to 1 mg/kg body weight in terms of the weight of each of the peptides. Alternatively, the blending amount may be 10 μg to 500 mg, more preferably 100 μg to 100 mg per 100 g of the food or drink although being not limited thereto. The intake amount for each ingestion of a food, for example, a functional food, can also be further reduced compared to the above amount, depending on the number of ingestions per day. The suitable intake amount can be further adjusted considering various factors.

The food or drink or the supplement according to the present invention may be further blended with a combination of other materials and compounds described below, which are considered to have brain function-improving actions:

Food ingredients such as, for example, ginkgo leaf extract, arachidonic acid (ARA), GABA, theanine, ceramide, caffeine, carnitine, α-glycerylphosphorylcholine (α-GPC), *Bacopa monniera*, DHA-bound phospholipids, phosphatidylserine (PS), phosphatidylcholine, St. John's wort, astaxanthin, niacin, pyrroloquinoline quinone (PQQ), and coenzyme Q10 (CoQ10);

Unsaturated fatty acids such as, for example, docosahexaenoic acid (DHA) and eicosapentaenoic acid (EPA);

Polyphenols such as, for example, resveratrol;

Chlorogenic acid and the like;

Catechins and the like.

The blending amount of these materials and compounds is within the known range in which efficacy is confirmed.

EXAMPLES

The present invention will be described below in further detail with reference to Examples. However, the scope of the invention is not limited to these Examples.

Example 1

Method for Enzymatically Preparing Peptides Asn-Ile-Pro-Pro-Leu-Thr-Gln-Thr-Pro-Val-Val-Val-Pro-Pro-Phe-Leu-Gln-Pro-Glu (NIPPLTQTPVVVPP-FLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLT QTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFP-PQSVL; SEQ ID NO: 3) by Hydrolysis of Casein Using Microorganism-Derived Enzyme 10 mg of cow milk-derived casein sodium was dispersed and dissolved in 1 ml of phosphate buffer solution of pH 7.0 to 7.3, and adjusted to a temperature of 50° C. to prepare a substrate solution. Each of the commercially available enzymes shown in Table 1 was added to the resultant substrate solution to a weight ratio of each enzyme/casein of 1/100 to 1/400, and then reacted at 50° C. for 4 hours, followed by adding a 10% aqueous trichloroacetic acid solution to a final concentration of 1% to the reaction solution to terminate the reaction. Subsequently, each peptide contained in the resultant solution was quantitated by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard.

The yield of the peptides of SEQ ID NOS: 1, 2, and 3 was roughly estimated by taking the β-casein concentration in the 10 mg/ml casein sodium solution used for the analysis to be 3 mg/ml and taking the molecular weight of β-casein to be 25,100, the molecular weight of SEQ ID NO: 1 to be 2086.4, the molecular weight of SEQ ID NO: 2 to be 2316.8, and the molecular weight of SEQ ID NO: 3 to be 2550.0.

The results shown in Table 1 demonstrated that Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQSVL; SEQ ID NO: 3) were obtained with high yields by the hydrolysis of casein using each of the enzymes having neutral protease or alkaline protease activity, derived from the genus *Bacillus* and the genus *Aspergillus*.

and adjusted to a temperature of 40° C. to prepare a substrate solution. Each of the commercially available enzymes shown in Table 2 was added to the resultant substrate solution to a weight ratio of each enzyme/casein of 1/200, and then reacted at 40° C. for 3 hours, followed by adding a 10% aqueous trichloroacetic acid solution to a final concentration of 1% to the reaction solution to terminate the reaction. Subsequently, each peptide contained in the resultant solution was quantitated by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard. The yield of each peptide was roughly estimated as described in Example 1.

The results shown in Table 2 demonstrated that Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQSVL; SEQ ID NO: 3) were little produced by the hydrolysis of casein using each of the enzymes having an acidic protease activity.

TABLE 1

(pH of neutral region)

| Origin | Enzyme name (product name) | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|
| *Bacillus licheniformis* | Protin SD-AY10[1] | 8.4 | 53.0 | 61.3 | 10.9 |
| *Aspergillus* sp. | Sumizyme MP[2] | 12.0 | 20.8 | 32.8 | 0.2 |
| *Aspergillus oryzae* | Sumizyme LP50[2] | 3.3 | 24.5 | 27.8 | 2.7 |
| *Bacillus licheniformis* | Protease P5459[3] | 4.5 | 22.8 | 27.3 | 3.9 |
| *Aspergillus melleus* | Protease P "amano" 3SD[1] | 2.9 | 24.3 | 27.2 | 1.2 |
| *Aspergillus oryzae* | Sumizyme FP[2] | 2.3 | 20.8 | 23.1 | 1.0 |
| *Aspergillus oryzae* | Proteax[1] | 5.5 | 15.3 | 20.8 | 0.1 |
| *Aspergillus oryzae* | Umamizyme G[1] | 3.9 | 16.1 | 20.0 | 0.4 |
| *Aspergillus oryzae* | Protease A "amano" SD[1] | 0.5 | 10.8 | 11.3 | 0.8 |
| *Aspergillus oryzae* | Protease M "amano" SD[1] | 0.1 | 2.8 | 2.9 | 1.0 |
| *Bacillus amyloliquefaciens* | Protin SD-NY10[1] | 0.1 | 0.1 | 0.1 | 0.0 |
| *Bacillus stearothermophilus* | Thermoase PC10F[1] | 0.0 | 0.0 | 0.0 | 0.0 |

[1] From Amano Enzyme Inc.,
[2] From SHINNIHON CHEMICALS Corporation,
[3] From Sigma-Aldrich Corporation Comparative Example 1

Method for Enzymatically Preparing Peptides Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQSVL; SEQ ID NO: 3) by Hydrolysis of Casein Using Acidic Protease 10 mg of cow milk-derived casein sodium was dispersed and dissolved in 1 ml of acetate buffer solution of pH 4.0,

TABLE 2

(pH of acidic region)

| Origin | Enzyme name (product name) | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|
| *Aspergillus saitoi* | Protease (P2143)[1] | 0.0 | 0.0 | 0.0 | 0.1 |
| *Rhizopus* sp. | Protease (P0107)[1] | 0.0 | 0.0 | 0.0 | 0.0 |
| porcine stomach mucosa | Pepsin (P7000)[1] | 0.0 | 0.0 | 0.0 | 0.4 |

[1] From Sigma-Aldrich Corporation

Comparative Example 2

Method for Enzymatically Preparing Peptides Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQSVL; SEQ ID NO: 3) by Hydrolysis of Casein Using Each of Mammal-Derived Pancreatin and Trypsin 10 mg of cow milk-derived casein sodium was dispersed and dissolved in 1 ml of phosphate buffer solution of pH 7.3, and adjusted to a temperature of 50° C. to prepare a substrate solution. Each of the commercially available enzymes pancreatin and trypsin shown in Table 3 was added to the resultant substrate solution to a weight ratio of each enzyme/casein of 1/200, and then reacted at 50° C. for 4 hours, followed by adding a 10% aqueous trichloroacetic acid solution to a final concentration of 1% to the reaction solution to terminate the reaction. Subsequently, each peptide contained in the resultant solution was quantitated by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard. The yield of each peptide was roughly estimated as described in Example 1.

The results shown in Table 3 demonstrated that Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLT QTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQSVL; SEQ ID NO: 3) were little produced by the hydrolysis of casein using each of pancreatin and trypsin, mammal-derived enzymes.

TABLE 3

| Origin | Enzyme name (product name) | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|
| porcine pancreas | Pancreatin (P1750)[1] | 0.3 | 6.5 | 6.8 | 0.0 |
| bovine pancreas | Trypsin (208-13954)[2] | 0.0 | 0.0 | 0.0 | 0.0 |

[1]From Sigma-Aldrich Corporation,
[2]From Wako Pure Chemical Industries Ltd.

Example 2

Study of Optimal Reaction Time for Production of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SWMHQP HQPLPPTVMFPPQSVL; SEQ ID NO: 3)

10 mg of cow milk-derived casein sodium was dispersed and dissolved in 1 ml of phosphate buffer solution of pH 7.3, and adjusted to a temperature of 50° C. to prepare a substrate solution. A *Bacillus licheniformis*-derived enzyme, Protin SD-AY10 (Amano Enzyme Inc.), was added to the resultant substrate solution to a weight ratio of the enzyme/casein of each of 1/200 and 1/1,000, and then reacted at 50° C. for 7 hours. During the reaction, the reaction solution was recovered over time every one hour. Upon the recovery, a 10% aqueous trichloroacetic acid solution was added to a final concentration of 1% to the reaction solution to terminate the reaction. Subsequently, each peptide contained in the resultant solution was quantitated by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard. The yield of each peptide was roughly estimated as described in Example 1.

Figure 2:
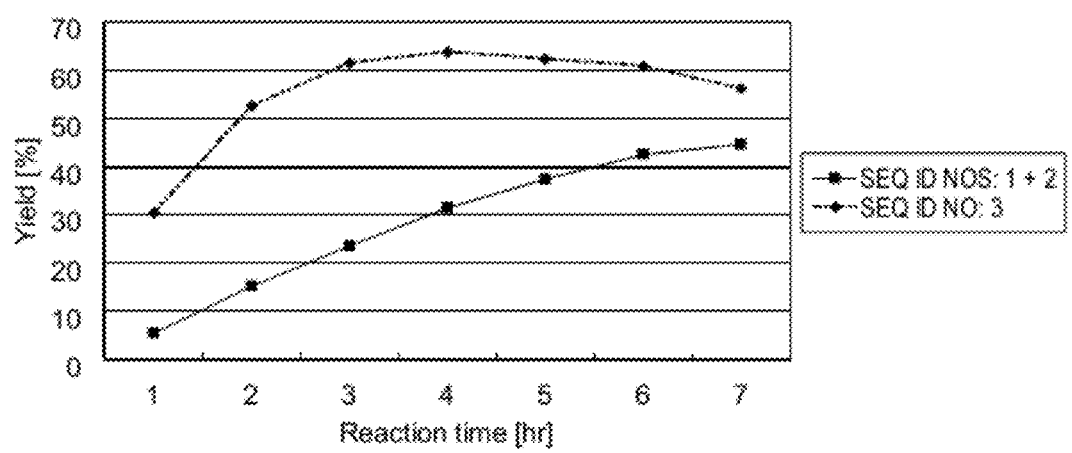
FIG. 2 is a graph showing the time course of the production yield of Asn-Ile-Pro-Pro-Leu-Thr-Gln-Thr-Pro-Val-Val-Val-Pro-Pro-Phe-Leu-Gln-Pro-Glu (NIPPLTQTPVVVPP-FLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2) and Ser-Trp-Met-His-Gln-Pro-His-Gln-Pro-Leu-Pro-Pro-Thr-Val-Met-Phe-Pro-Pro-Gln-Ser-Val-Leu (SWMHQPHQ-PLPPT VMFPPQSVL; SEQ ID NO: 3) when a *Bacillus licheniformis*-derived enzyme, Protin SD-AY10 (from Amano Enzyme Inc.), was added to a phosphate buffer solution (pH: 7.0 to 7.3) containing cow milk casein sodium to a weight ratio of enzyme/casein of 1/1,000 for hydrolysis reaction.

From the results shown in Table 4, FIG. 1, Table 5 and FIG. 2, the total of the yields of Asn-Ile-Pro-Pro-Leu-Thr-Gln-Thr-Pro-Val-Val-Val-Pro-Pro-Phe-Leu-Gln-Pro-Glu (NIPPLTQT PVVVPPFLQPE; SEQ ID NO: 1) and Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2) had the maximum values 4 hours after the start of reaction when the enzyme was added at the weight ratio of enzyme/casein of 1/200 (FIG. 1). Similarly, the yield of Ser-Trp-Met-His-Gln-Pro-His-Gln-Pro-Leu-Pro-Pro-Thr-Val-Met-Phe-Pro-Pro-Gln-Ser-Val-Leu (SWMHQPHQPLPPTVMFPPQS VL; SEQ ID NO: 3) had the maximum value 4 hours after the start of reaction when the enzyme was added at the weight ratio of enzyme/casein of 1/1,000 (FIG. 2). The above demonstrated that these peptides were obtained with high yields by terminating the reaction in a short time.

TABLE 4

(Amount of enzyme added: 1/200 of total)

| Origin | Enzyme name (product name) | Reaction time [hr] | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|---|
| *Bacillus licheniformis* | Protin SD-AY10 | 1 | 0.9 | 12.0 | 12.9 | 17.9 |
| | | 2 | 1.7 | 17.7 | 19.5 | 9.9 |
| | | 3 | 2.8 | 19.9 | 22.7 | 6.3 |

TABLE 4-continued (Amount of enzyme added: 1/200 of total)

| Origin | Enzyme name (product name) | Reaction time [hr] | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|---|
| | | 4 | 8.4 | 53.0 | 61.3 | 10.9 |
| | | 5 | 10.5 | 47.8 | 58.3 | 8.1 |
| | | 6 | 11.4 | 42.0 | 53.4 | 5.6 |
| | | 7 | 12.7 | 38.2 | 50.9 | 4.2 |

TABLE 5

(Amount of enzyme added: 1/1,000 of total)

| Origin | Enzyme name (product name) | Reaction time [hr] | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|---|
| *Bacillus licheniformis* | Protin SD-AY10 | 1 | 0.5 | 4.7 | 5.3 | 30.4 |
| | | 2 | 0.7 | 14.5 | 15.2 | 52.4 |
| | | 3 | 0.8 | 22.7 | 23.5 | 61.5 |
| | | 4 | 1.2 | 30.2 | 31.4 | 63.9 |
| | | 5 | 1.6 | 35.7 | 37.3 | 62.4 |
| | | 6 | 2.0 | 40.4 | 42.4 | 60.8 |
| | | 7 | 2.4 | 42.2 | 44.6 | 56.0 |

Example 3

Study of Optimal Reaction Time for Production of Asn-Ile-Pro-Pro-Leu-Thr-Gln-Thr-Pro-Val-Val-Val-Pro-Pro-Phe-Leu-Gln-Pro-Glu (SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (SEQ ID NO: 2), and Ser-Trp-Met-His-Gln-Pro-His-Gln-Pro-Leu-Pro-Pro-Thr-Val-Met-Phe-Pro-Pro-Gln-Ser-Val-Leu (SEQ ID NO: 3)

10 mg of cow milk-derived casein sodium was dispersed and dissolved in 1 ml of phosphate buffer solution of pH 7.0 or 8.0, and adjusted to a temperature of 50° C. to prepare a substrate solution. An *Aspergillus* sp.-derived enzyme, Sumizyme MP (from Shinnihon Chemicals Corporation), was added to the resultant substrate solution to a weight ratio of the enzyme/casein of 1/200, and then reacted at 50° C. for 7 hours. During the reaction, the reaction solution was recovered over time every one hour. Upon the recovery, a 10% aqueous trichloroacetic acid solution was added to a final concentration of 1% to the reaction solution to terminate the reaction. Subsequently, each peptide contained in the resultant solution was quantitated by, with the use of a high-performance liquid chromatograph triple quadrupole mass spectrometer (LC/MS/MS, Waters TQD), separating the components by gradient analysis using a reverse phase ODS column as a separation column and a 0.1% formic acid aqueous solution and 0.1% formic acid-containing acetonitrile as eluents, detecting each peptide with the mass spectrometer, and calculating the content thereof using a calibration curve prepared using a synthetic peptide as a standard. The yield of each peptide was roughly estimated as described in Example 1.

Figure 3:
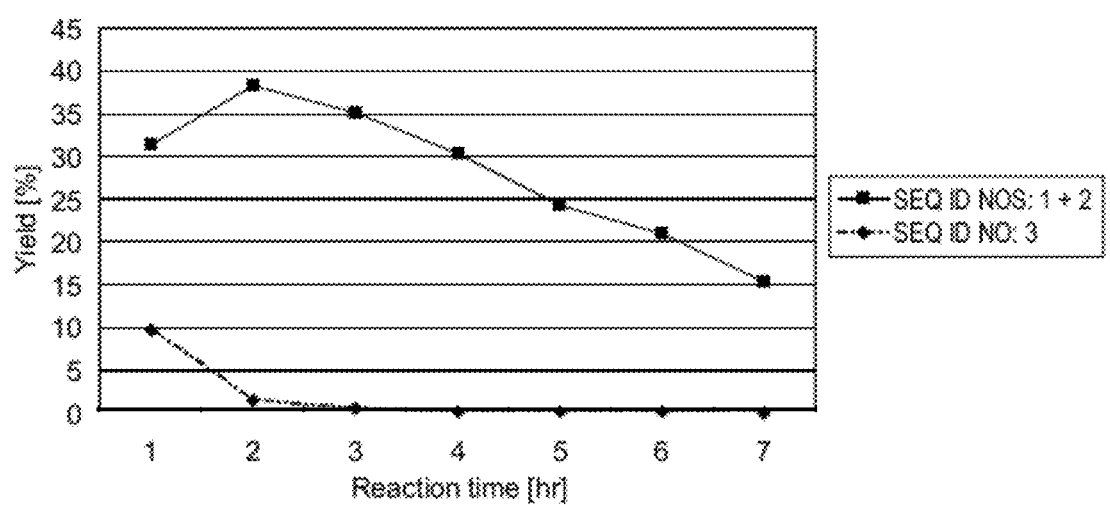
FIG. 3 is a graph showing the time course of the production yield of Asn-Ile-Pro-Pro-Leu-Thr-Gln-Thr-Pro-Val-Val-Val-Pro-Pro-Phe-Leu-Gln-Pro-Glu (NIPPLTQTPVVVPP-FLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2) and Ser-Trp-Met-His-Gln-Pro-His-Gln-Pro-Leu-Pro-Pro-Thr-Val-Met-Phe-Pro-Pro-Gln-Ser-Val-Leu (SWMHQPHQ-PLPPTV MFPPQSVL; SEQ ID NO: 3) when an *Aspergillus* sp.-derived enzyme, Sumizyme MP (from Shinnihon Chemicals Corporation), was added to a phosphate buffer solution (pH: 7.0) containing cow milk casein sodium to a weight ratio of enzyme/casein of 1/200 for hydrolysis reaction.
Figure 4:
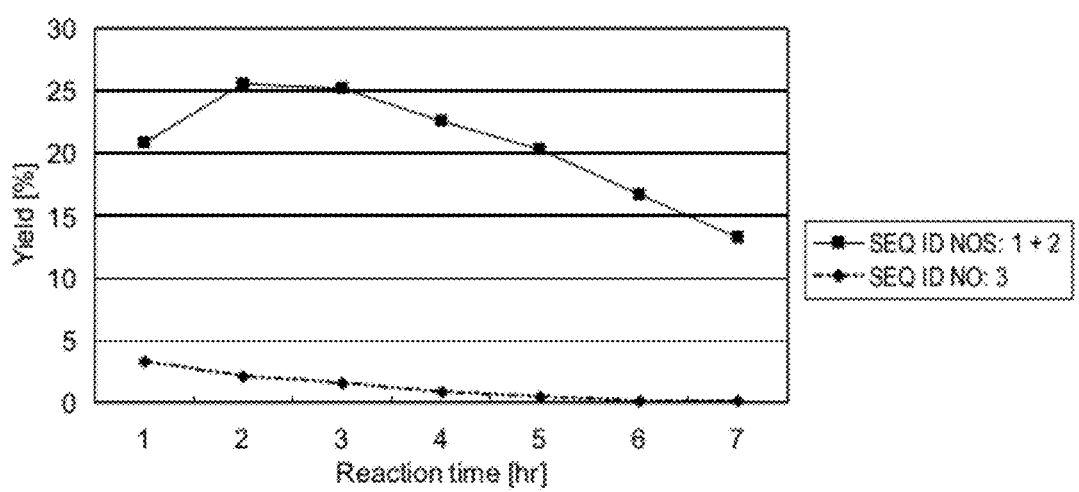
FIG. 4 is a graph showing the time course of the production yield of Asn-Ile-Pro-Pro-Leu-Thr-Gln-Thr-Pro-Val-Val-Val-Pro-Pro-Phe-Leu-Gln-Pro-Glu (NIPPLTQTPVVVPP-FLQPE; SEQ ID NO: 1), Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPPFLQPEVM; SEQ ID NO: 2) and Ser-Trp-Met-His-Gln-Pro-His-Gln-Pro-Leu-Pro-Pro-Thr-Val-Met-Phe-Pro-Pro-Gln-Ser-Val-Leu (SWMHQPHQ-PLPPTV MFPPQSVL; SEQ ID NO: 3) when an *Aspergillus* sp.-derived enzyme, Sumizyme MP (from Shinnihon Chemicals Corporation), was added to a phosphate buffer solution (pH: 8.0) containing cow milk casein sodium to a weight ratio of enzyme/casein of 1/200 for hydrolysis reaction.

From the results shown in Table 6, FIG. 3, Table 7 and FIG. 4, the total of the yields of Asn-Ile-Pro-Pro-Leu-Thr-Gln-Thr-Pro-Val-Val-Val-Pro-Pro-Phe-Leu-Gln-Pro-Glu (SEQ ID NO: 1) and Asn-Ile-Pro-Pro-Leu-Thr-Gln-Thr-Pro-Val-Val-Val-Pro-Pro-Phe-Leu-Gln-Pro-Glu-Val-Met (SEQ ID NO: 2) had the maximum values 2 to 3 hours after the start of reaction in both the cases of pH 7.0 and pH 8.0. Similarly, the yield of Ser-Trp-Met-His-Gln-Pro-His-Gln-Pro-Leu-Pro-Pro-Thr-Val-Met-Phe-Pro-Pro-Gln-Ser-Val-Leu (SEQ ID NO: 3) had the maximum value one hour after the start of reaction; however, it decreased with the lapse of time. The above demonstrated that these peptides were obtained with high yields by terminating the reaction in a short time.

TABLE 6

(Reaction pH: 7.0)

| Origin | Enzyme name (product name) | Reaction time [hr] | SEQ ID NO: 1 yield [%] | SEQ ID NO: 2 yield [%] | SEQ ID NOS: 1 + 2 yield [%] | SEQ ID NO: 3 yield [%] |
|---|---|---|---|---|---|---|
| *Aspergillus* sp. | Sumizyme MP | 1 | 4.9 | 26.5 | 31.4 | 9.8 |
| | | 2 | 8.9 | 29.4 | 38.3 | 1.5 |
| | | 3 | 11.1 | 24.1 | 35.2 | 0.5 |
| | | 4 | 10.5 | 19.8 | 30.3 | 0.2 |
| | | 5 | 10.4 | 13.9 | 24.3 | 0.1 |
| | | 6 | 9.0 | 12.0 | 21.0 | 0.1 |
| | | 7 | 7.5 | 7.9 | 15.4 | 0.0 |

TABLE 7

| | | | (Reaction pH: 8.0) | | | |
|---|---|---|---|---|---|---|
| Origin | Enzyme name (product name) | Reaction time [hr] | SEQ ID NO: 1 yield [%] | SEQ ID NO: 2 yield [%] | SEQ ID NOS: 1 + 2 yield [%] | SEQ ID NO: 3 yield [%] |
| Aspergillus sp. | Sumizyme MP | 1 | 8.4 | 12.5 | 20.9 | 3.3 |
| | | 2 | 14.2 | 11.4 | 25.6 | 2.1 |
| | | 3 | 16.4 | 8.7 | 25.2 | 1.5 |
| | | 4 | 15.7 | 6.9 | 22.6 | 0.9 |
| | | 5 | 14.8 | 5.5 | 20.3 | 0.5 |
| | | 6 | 12.6 | 4.1 | 16.6 | 0.1 |
| | | 7 | 10.0 | 3.2 | 13.2 | 0.1 |

Example 4

Amnesia-Preventing Action of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1)

Figure 5:
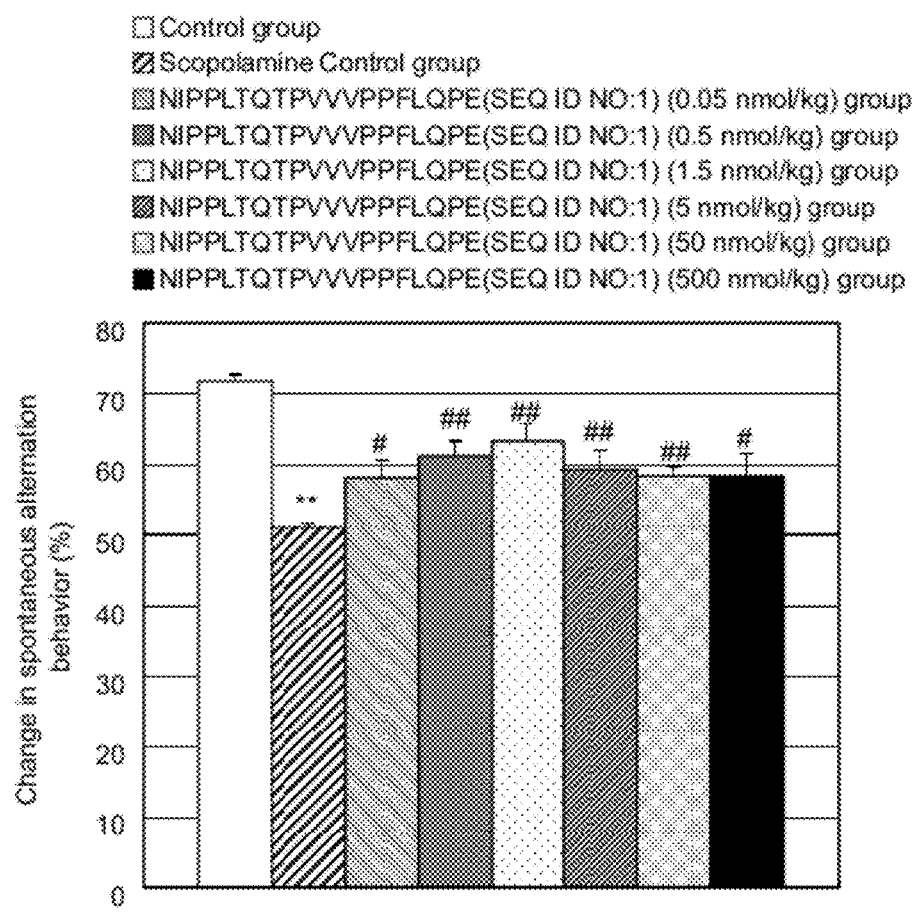
FIG. 5 is a graph showing an effect of preventing scopolamine-induced amnesia of the peptide Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1). Water (control), scopolamine alone, or 0.05 nmol/kg body weight, 0.5 nmol/kg body weight, 1.5 nmol/kg body weight, 5 nmol/kg body weight, 50 nmol/kg body weight, and 500 nmol/kg body weight of NIPPLTQTPVVVPPFLQPE (SEQ ID NO: 1) with scopolamine was administered to mice, and the amnesia-preventing effects thereof were evaluated by a method as described in Example 4. The vertical axis of FIG. 4 represents change in spontaneous alternation behavior (%). In the graph, the spontaneous alternation behavior (%) for a control group, a scopolamine control group, and 0.05 nmol/kg body weight, 0.5 nmol/kg body weight, 1.5 nmol/kg body weight, 5 nmol/kg body weight, 50 nmol/kg body weight, and 500 nmol/kg body weight of NIPPLTQTPV-VVPPFLQPE (SEQ ID NO: 1)-administered groups are shown in order from the left. To confirm whether amnesia is induced, the significance of difference between the water-administered control group and the scopolamine alone-administered scopolamine control group was tested by Student's t-test. ** indicates p<0.01 relative to the water-administered control group. The significance of difference between the NIPPLTQTPVVVPPFLQPE (SEQ ID NO: 1)-administered group and the scopolamine control group was tested by Dunnett's multiple comparison test. # indicates p<0.05 relative to the scopolamine control group. ## indicates p<0.01 relative to the scopolamine control group.

Male ddY mice (about 7 weeks old) were used (n=15 to 75), and provided with food and water ad libitum. Asn-Ile-Pro-Pro-Leu-Thr-Gln-Thr-Pro-Val-Val-Val-Pro-Pro-Phe-Leu-Gln-Pro-Glu (SEQ ID NO: 1) was used as a test substance in amounts of 0.05 nmol/kg body weight (0.1 µg/kg body weight), 0.5 nmol/kg body weight (1 µg/kg body weight), 1.5 nmol/kg body weight (3 µg/kg body weight), 5 nmol/kg body weight (10 µg/kg body weight), 50 nmol/kg body weight (100 µg/kg body weight), and 500 nmol/kg body weight (1,000 µg/kg body weight). The test substance was administered as a single dose orally to mice 60 minutes before performing a Y-shaped maze test for evaluating spontaneous alternation behavior. Thirty minutes before performing the Y-shaped maze test, scopolamine was subcutaneously administered in an amount of 1 mg/kg body weight into the back to induce brain dysfunction (memory disorder and/or cognition disorder) in mice. In the Y-shaped maze test, as an experiment device, a Y-shaped maze was used in which the length for each arm was 40 cm; the wall height was 12 cm; the floor width was 3 cm; the upper part width was 10 cm; and three arms were connected to each other at an angle of 120°. Each mouse was placed in the end of any of the alms of the Y-shaped maze and allowed to explore freely in the maze over 8 minutes, and the sequence of the arms to which the mouse moved was recorded. The number of movements of the mouse to the arms within the measurement time was counted and used as the total number of entries; in the sequence, the combination in which three different arms were selected in succession (for example, with the three arms respectively called A, B, and C, if the sequence of the arms entered is ABCBACACB, the count is 4 inclusive of overlapping) was investigated, and the count number was used as the number of spontaneous alternation behaviors. The change in spontaneous alternation behavior (%) was calculated by dividing the number of spontaneous alternation behaviors by a number obtained by subtracting 2 from the total number of entries, and multiplying the resultant number by 100, and the percentage was used as an indicator of the spontaneous alternation behavior. A higher value of the indicator suggests better maintenance of short-term memory. The measured values were expressed as mean±standard error for each group. The significance of difference between the control group and the scopolamine control group was tested by Student's t-test. The significance of difference between the scopolamine control group and the NIPPLTQTPVVVPPFLQPE (SEQ ID NO: 1)-administered group was tested by Dunnett's multiple comparison test after one-way analysis of variance. The results are shown in FIG. 5. NIPPLTQTPVVVPPFLQPE (SEQ ID NO: 1) was shown to have an amnesia-preventing action in the range of 0.05 nmol/kg body weight to 500 nmol/kg body weight (0.1 µg/kg body weight to 1,000 µg/kg body weight).

Example 5

Figure 6:
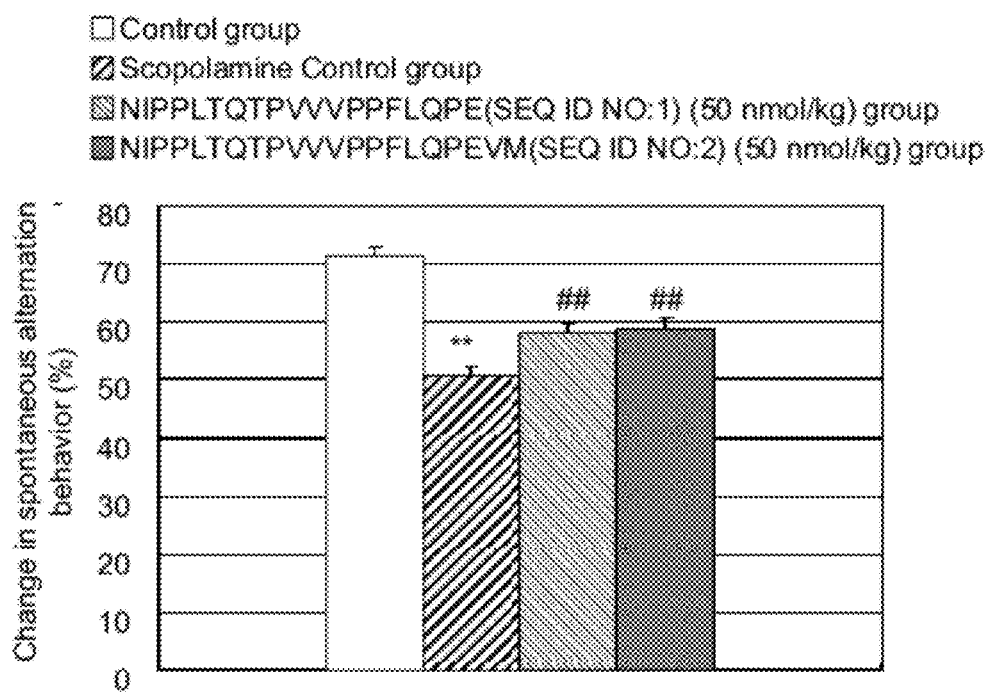
FIG. 6 is a graph showing an effect of preventing scopolamine-induced amnesia of the peptide Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1), or Asn-Ile-Pro-Pro-Leu-Thr-Gln-Thr-Pro-Val-Val-Val-Pro-Pro-Phe-Leu-Gln-Pro-Glu-Val-Met (NIPPLTQTPVVVPP-FLQPEVM; SEQ ID NO: 2). Water (control), scopolamine alone, or 50 nmol/kg body weight of NIPPLTQTPVVVPP-FLQPE (SEQ ID NO: 1), or 50 nmol/kg body weight of NIPPLTQTPVVVPPFLQPEVM (SEQ ID NO: 2) with scopolamine was administered to mice, and the amnesia-preventing effects thereof were evaluated by a method as described in Example 5. The vertical axis of FIG. 5 represents change in spontaneous alternation behavior (%). To confirm whether amnesia is induced, the significance of difference between the water-administered control group and the scopolamine alone-administered scopolamine control group was tested by Student's t-test. ** indicates p<0.01 relative to the water-administered control group. The significance of difference between each of the peptide-administered groups and the scopolamine control group was tested by Dunnett's multiple comparison test. ## indicates p<0.01 relative to the scopolamine control group.

Amnesia-Preventing Action of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1)-Related Peptide Male ddY mice (about 7 weeks old) were used (n=15 to 45), and provided with food and water ad libitum. As a test substance, 50 nmol/kg body weight (100 µg/kg body weight) of Asn-Ile-Pro-Pro-Leu-Thr-Gln-Thr-Pro-Val-Val-Val-Pro-Pro-Phe-Leu-Gln-Pro-Glu (SEQ ID NO: 1) or 50 nmol/kg body weight (120 µg/kg body weight) of Asn-Ile-Pro-Pro-Leu-Thr-Gln-Thr-Pro-Val-Val-Val-Pro-Pro-Phe-Leu-Gln-Pro-Glu-Val-Met (NIPPLT QTPVVVPPFLQPEVM; SEQ ID NO: 2) was used. The test substance was administered as a single dose orally to mice 60 minutes before performing a Y-shaped maze test for evaluating spontaneous alternation behavior. Thirty minutes before performing the Y-shaped maze test, scopolamine was subcutaneously administered in an amount of 1 mg/kg body weight into the back to induce brain dysfunction (memory disorder and/or cognition disorder) in mice. In the Y-shaped maze test, as an experiment device, a Y-shaped maze was used in which the length for each aim was 40 cm; the wall height was 12 cm; the floor width was 3 cm; the upper part width was 10 cm; and three arms were connected to each other at an angle of 120°. Each mouse was placed in the end of any of the arms of the Y-shaped maze and allowed to explore freely in the maze over 8 minutes, and the sequence of the arms to which the mouse moved was recorded. The number of movements of the mouse to the arms within the measurement time was counted and used as the total number of entries; in the sequence, the combination in which three different arms were selected in succession (for example, with the three arms respectively called A, B, and C, if the sequence of the arms entered is ABCBACACB, the count is 4 inclusive of overlapping) was investigated, and the count number was used as the number of spontaneous alternation behaviors. The change in spontaneous alternation behavior (%) was calculated by dividing the number of spontaneous alternation behaviors by a number obtained by subtracting 2 from the total number of entries, and multiplying the resultant number by 100, and the percentage was used as an indicator of the spontaneous alternation behavior. A higher value of the indicator suggests better maintenance of short-term memory. The measured values were expressed as mean±standard error for each group. The significance of difference between the control group and the scopolamine control group was tested by Student's t-test. The significance of difference between the scopolamine control group and each peptide-administered group was tested by Dunnett's multiple comparison test after one-way analysis of variance. The results are shown in FIG. 6. NIPPLTQTPVVVPP-FLQPE (SEQ ID NO: 1) and NIPPLTQTPVVVPP-FLQPEVM (SEQ ID NO: 2) were shown to have an amnesia-preventing action at 50 nmol/kg body weight (100 µg/kg body weight) and 50 nmol/kg body weight (120 µg/kg body weight), respectively.

Example 6

Memory-Enhancing Action of Asn-Ile-Pro-Pro-Leu-Thr-Gln-Thr-Pro-Val-Val-Val-Pro-Pro-Phe-Leu-Gln-Pro-Glu (NIPPLTQTPVVVPPFLQPE; SEQ ID NO: 1)

Figure 7:
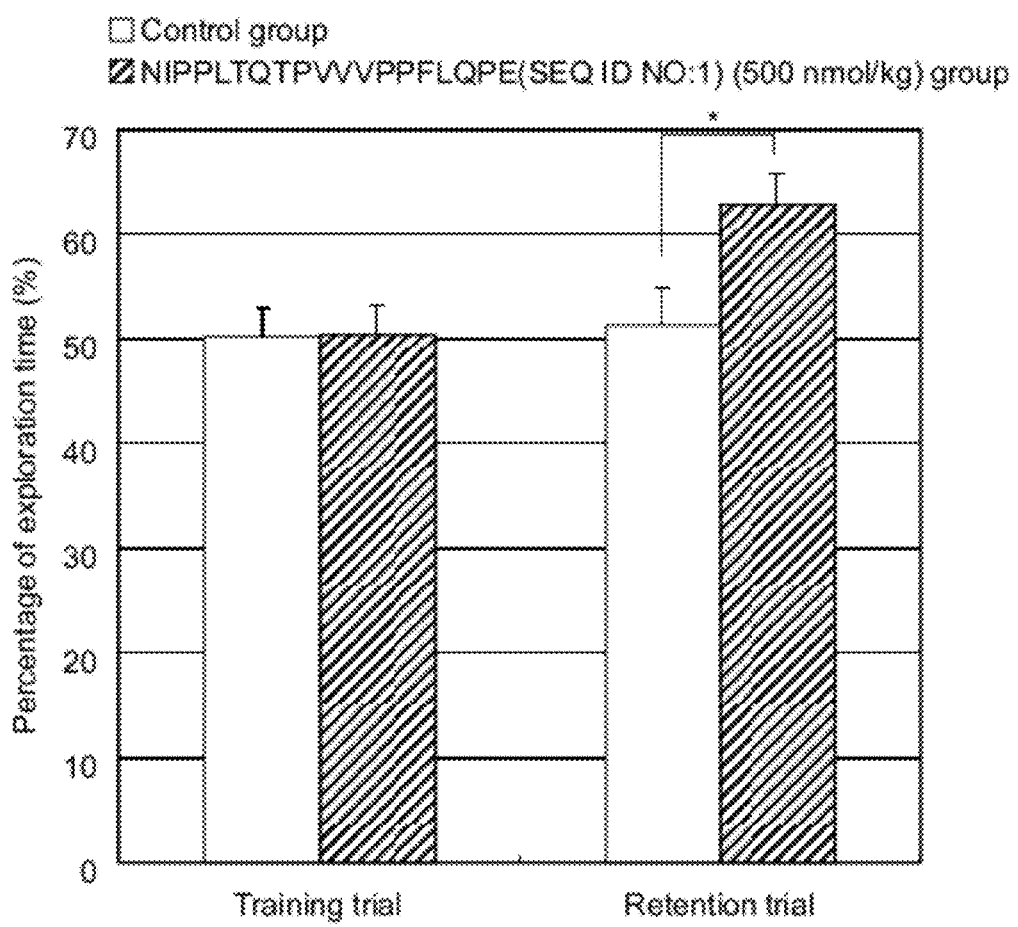
FIG. 7 is a graph showing a memory-enhancing effect of the peptide Asn-Ile-Pro-Pro-Leu-Thr-Gln-Thr-Pro-Val-Val-Val-Pro-Pro-Phe-Leu-Gln-Pro-Glu (SEQ ID NO: 1). Water (control) or 500 nmol/kg of NIPPLTQTPVVVPPFLQPE (SEQ ID NO: 1) was administered to mice, and the memory-enhancing effects thereof were evaluated by a method as described in Example 6. The vertical axis of FIG. 7 represents the percentage of exploration time. The significance of difference between the control group and the peptide group was tested for the percentage of exploration time by Student's t-test. * indicates p<0.05 relative to the water-administered control group.

Male ddY mice (about 7 weeks old) were used (n=14 to 15), and provided with food and water ad libitum. As a test substance, 500 nmol/kg body weight (1,000 µg/kg body weight) of Asn-Ile-Pro-Pro-Leu-Thr-Gln-Thr-Pro-Val-Val-Val-Pro-Pro-Phe-Leu-Gln-Pro-Glu (SEQ ID NO: 1) was used. The test substance was administered as a single dose orally to mice 60 minutes before performing a novel object recognition test for evaluating memory retention. In the novel object recognition test, a 30×30×30 cm box was used as an experiment device. As a conditioning operation, a mouse was placed in an experiment device in which a floorcloth was laid for 5 minutes, and allowed to explore freely in the device. A training trial was performed the day following the conditioning operation. In the training trial, 2 out of 3 objects were selected and placed in the experiment device (the objects were placed at positions 8 cm from the walls on the both sides along the central line of the floor, and the positions were called X1 and X2.). For the selection of the objects to be placed, the objects were randomly selected in advance to prevent bias among the animals and among the groups. Sixty minutes after orally administering the test substance or water, a mouse was placed in the experiment device for 5 minutes, and the time (second) was measured during which the mouse explored by approaching each object to be within 1 cm therefrom. A retention trial was performed 48 hours after the training trial. In the retention trial, 2 objects were placed in the experiment device as in the training trial; however, 1 of the objects was substituted for a different object (a novel object) from that used in the training trial, and the position thereof was called Y. (For example, when an object A was placed in X1 and an object B in X2 in the training trial, an object C was placed in place of the object A in the retention trial, and the position thereof was called Y.) In the training trial and the retention trial, the time (second) was measured during which each mouse explored by approaching each object to be within 1 cm therefrom. (However, the state in which a mouse rides on an object is excluded.) The percentages of the times were determined during which two objects were explored in each of the training trial and the retention trial. The percentage (%) of the exploration time for each object was expressed as mean±standard error for each of the groups. The significance of difference between the control group and the peptide group was tested by Student's t-test for the percentage of the exploration time for the novel object (the object placed at Y) in the retention trial and the percentage of the exploration time for the object (the object placed at X1 or X2) placed at the position at which the novel object is placed in the training trial. The results are shown in FIG. 7. NIPPLTQT-PVVVPPFLQPE (SEQ ID NO: 1) was shown to have a memory-enhancing action at 500 nmol/kg body weight (1,000 µg/kg body weight).

Example 7

Amnesia-Preventing Action of Ser-Trp-Met-His-Gln-Pro-His-Gln-Pro-Leu-Pro-Pro-Thr-Val-Met-Phe-Pro-Pro-Gln-Ser-Val-Leu (SWMHQPHQ-PLPPTVMFPPQSVL; SEQ ID NO: 3)

Figure 8:
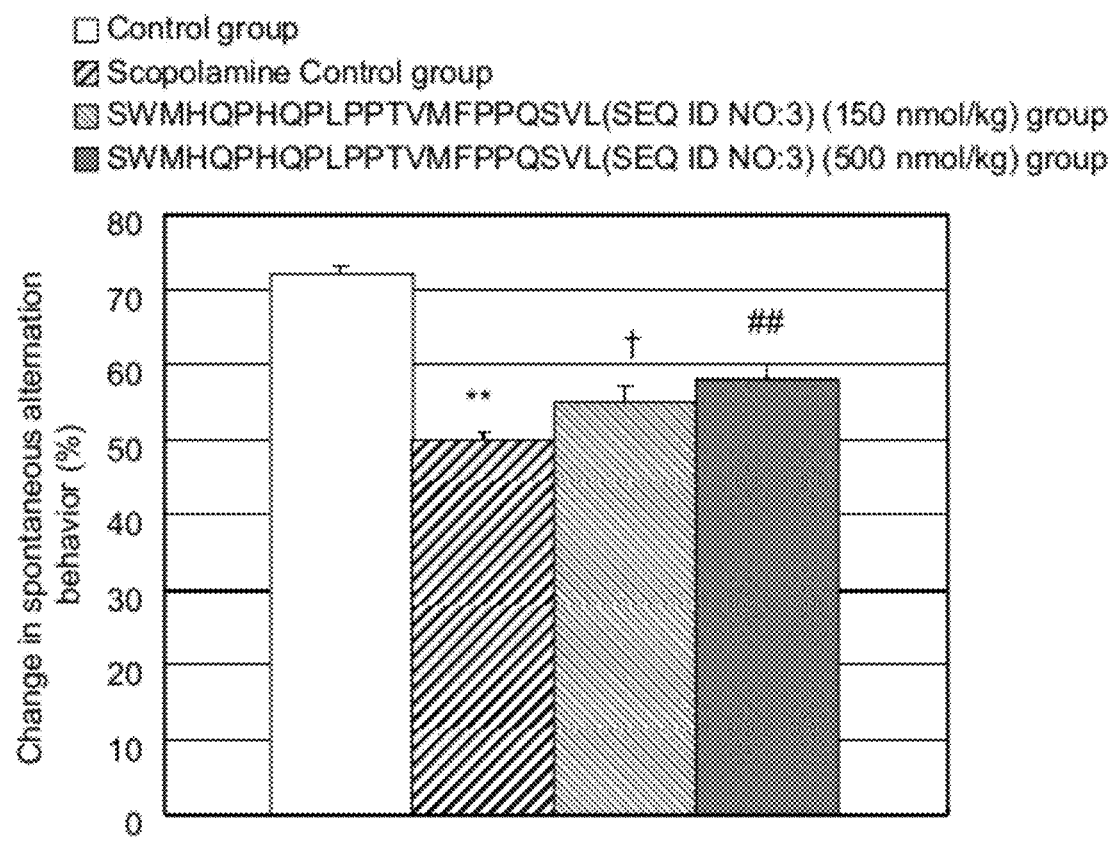
FIG. 8 is a graph showing an effect of preventing scopolamine-induced amnesia of the peptide Ser-Trp-Met-His-Gln-Pro-His-Gln-Pro-Leu-Pro-Pro-Thr-Val-Met-Phe-Pro-Pro-Gln-Ser-Val-Leu (SEQ ID NO: 3). Water (control), scopolamine alone, or 150 nmol/kg body weight or 500 nmol/kg body weight of SWMHQPHQPLPPTVMFP-PQSVL (SEQ ID NO: 3) with scopolamine was administered to mice, and the amnesia-preventing effects thereof were evaluated by a method as described in Example 7. To confirm whether amnesia is induced, the significance of difference between the water-administered control group and the scopolamine alone-administered scopolamine control group was tested by Student's t-test. ** indicates p<0.01 relative to the water-administered control group. The significance of difference between each of the peptide-administered groups and the scopolamine control group was tested by Student's t-test. ## indicates p<0.01 relative to the scopolamine control group, and † indicates p<0.1.

Male ddY mice (about 7 weeks old) were used (n=15 to 30), and provided with food and water ad libitum. As a test substance, Ser-Trp-Met-His-Gln-Pro-His-Gln-Pro-Leu-Pro-Pro-Thr-Val-Met-Phe-Pro-Pro-Gln-Ser-Val-Leu (SEQ ID NO: 3) was used at 150 nmol/kg body weight (380 µg/kg body weight) and 500 nmol/kg body weight (1,280 µg/kg body weight). The test substance was administered as a single dose orally to mice 60 minutes before performing a Y-shaped maze test for evaluating spontaneous alternation behavior. Thirty minutes before performing the Y-shaped maze test, scopolamine was subcutaneously administered in an amount of 1 mg/kg body weight into the back to induce brain dysfunction (memory disorder and/or cognition disorder) in mice. In the Y-shaped maze test, as an experiment device, a Y-shaped maze was used in which the length for each arm was 40 cm; the wall height was 12 cm; the floor width was 3 cm; the upper part width was 10 cm; and three arms were connected to each other at an angle of 120°. Each mouse was placed in the end of any of the arms of the Y-shaped maze and allowed to explore freely in the maze over 8 minutes, and the sequence of the arms to which the mouse moved was recorded. The number of movements of the mouse to the arms within the measurement time was counted and used as the total number of entries; in the sequence, the combination in which three different arms were selected in succession (for example, with the three arms respectively called A, B, and C, if the sequence of the arms entered is ABCBACACB, the count is 4 inclusive of overlapping) was investigated, and the count number was used as the number of spontaneous alternation behaviors. The change in spontaneous alternation behavior (%) was calculated by dividing the number of spontaneous alternation behaviors by a number obtained by subtracting 2 from the total number of entries, and multiplying the resultant number by 100, and the percentage was used as an indicator of the spontaneous alternation behavior. A higher value of the indicator suggests better maintenance of short-term memory. The measured values were expressed as mean±standard error for each group. The significance of difference between the control group and the scopolamine control group was tested by Student's t-test. The significance of difference between the scopolamine control group and the SWMHQPHQPLPPTVMFPPQSVL (SEQ ID NO: 3)-administered group was tested by Student's t-test. The results are shown in FIG. 8. SWMHQPHQPLPPTVMFPPQSVL (SEQ ID NO: 3) was shown to have an amnesia-preventing action at 150 nmol/kg body weight to 500 nmol/kg body weight (380 µg/kg body weight to 1,280 µg/kg).

According to the present invention, a new peptide for improving brain function is provided, which is obtained by the enzymatic hydrolysis using milk casein safe as a food as a raw material. The peptide is useful for ameliorating or improving symptoms of hypomnesia especially because it has the effect of improving or preventing amnesia.

It is apparent that the present invention can be carried out in embodiments that are not specifically mentioned in the above descriptions or in the Examples. Therefore, modifications or changes to the present invention can be made.

Thus, such modifications or changes fall within the scope of the claims of the present invention.

All publications, patents, and patent applications cited herein are incorporated herein by reference in their entirety.

peptide consisting of the amino acid sequence shown in SEQ ID NO: 1, the peptide consisting of the amino acid sequence shown in SEQ ID NO: 2, or a mixture comprising the peptides.

What is claimed is:

1. A method for preparing a peptide for improving brain function, comprising:

hydrolyzing milk casein with an enzymatic catalyst comprising a protease from a microorganism belonging to either the genus *Bacillus* or the genus *Aspergillus*, but not both, to produce a hydrolysate comprising:

(i) a peptide consisting of the amino acid sequence shown in SEQ ID NO: 1;

(ii) a peptide consisting of the amino acid sequence shown in SEQ ID NO: 2; or (iii) a mixture of the peptides of (i) and (ii), wherein the protease is selected from the group consisting of Protin SD-AY10, Sumizyme MP, Sumizyme LP50, Protease P5459, Protease P "amano" 3SD, Sumizyme FP, Proteax, and Umamizyme G; and isolating the peptide consisting of the amino acid sequence shown in SEQ ID NO: 1, the peptide consisting of the amino acid sequence shown in SEQ ID NO: 2, or a mixture comprising the peptides.

2. The method according to claim 1, further comprising concentrating the peptide consisting of the amino acid sequence shown in SEQ ID NO: 1, the peptide consisting of the amino acid sequence shown in SEQ ID NO: 2, or the mixture comprising the peptides.

3. The method according to claim 1, wherein the protease is a neutral protease or an alkaline protease.

4. The method according to claim 1, wherein the microorganism is selected from the group consisting of *Bacillus licheniformis*, *Aspergillus sp.*, *Aspergillus oryzae*, and *Aspergillus melleus*.

5. The method according to claim 1, wherein the milk casein is cow milk casein.

6. The method according to claim 1, wherein the method further comprises isolating the peptide consisting of the amino acid sequence shown in SEQ ID NO: 3, or a mixture comprising at least two of the peptides consisting of the amino acid sequence shown in SEQ ID NO: 1, the amino acid sequence shown in SEQ ID NO: 2, and the amino acid sequence shown in SEQ ID NO: 3.

7. The method according to claim 6, further comprising concentrating the peptide consisting of the amino acid sequence shown in SEQ ID NO: 3, or the mixture comprising at least two of the peptides consisting of the amino acid sequence shown in SEQ ID NO: 1, the amino acid sequence shown in SEQ ID NO: 2, and the amino acid sequence shown in SEQ ID NO: 3.

8. The method according to claim 1, wherein the enzymatic catalyst further comprises an enzyme having an activity to produce the N-E peptide or a variant peptide thereof comprising deletion, substitution, or addition of one or two amino acid residues from casein, or the N-EVM peptide or a variant thereof comprising deletion, substitution, or addition of one or two amino acid residues from casein, or the N-E peptide from the N-EVM peptide.

9. The method according to claim 1, wherein the enzymatic catalyst is immobilized on a support.

10. The method according to claim 1, wherein the hydrolysis of the milk casein is carried out using milk.

11. The method according to claim 1, wherein weight ratio of the enzyme/milk casein is 1/100 to 1/1,000.

12. The method according to claim 1, further comprising inactivating the enzymatic catalyst.

13. The method of claim 1, in which the hydrolysis is carried out for about 1 to about 7 hours.

* * * * *

UNITED STATES PATENT AND TRADEMARK OFFICE
CERTIFICATE OF CORRECTION

PATENT NO. : 9,523,109 B2
APPLICATION NO. : 13/495581
DATED : December 20, 2016
INVENTOR(S) : Naoto Uchida et al.

Page 1 of 1

It is certified that error appears in the above-identified patent and that said Letters Patent is hereby corrected as shown below:

(73) Assignee should read: ASAHI GROUP HOLDINGS, LTD., Tokyo (JP)

Signed and Sealed this
Eleventh Day of April, 2017

Michelle K. Lee
*Director of the United States Patent and Trademark Office*

```
                          SEQUENCE LISTING

<160> NUMBER OF SEQ ID NOS: 3

<210> SEQ ID NO 1
<211> LENGTH: 19
<212> TYPE: PRT
<213> ORGANISM: Artificial
<220> FEATURE:
<223> OTHER INFORMATION: Peptide derived from bovine casein

<400> SEQUENCE: 1

Asn Ile Pro Pro Leu Thr Gln Thr Pro Val Val Val Pro Pro Phe Leu
1               5                   10                  15

Gln Pro Glu

<210> SEQ ID NO 2
<211> LENGTH: 21
<212> TYPE: PRT
<213> ORGANISM: Artificial
<220> FEATURE:
<223> OTHER INFORMATION: Peptide derived from bovine casein

<400> SEQUENCE: 2

Asn Ile Pro Pro Leu Thr Gln Thr Pro Val Val Val Pro Pro Phe Leu
1               5                   10                  15

Gln Pro Glu Val Met
            20

<210> SEQ ID NO 3
<211> LENGTH: 22
<212> TYPE: PRT
<213> ORGANISM: Artificial
<220> FEATURE:
<223> OTHER INFORMATION: Peptide derived from bovine casein

<400> SEQUENCE: 3

Ser Trp Met His Gln Pro His Gln Pro Leu Pro Pro Thr Val Met Phe
1               5                   10                  15

Pro Pro Gln Ser Val Leu
            20
```